US011344287B2

(12) United States Patent
Taylor et al.

(10) Patent No.: US 11,344,287 B2
(45) Date of Patent: May 31, 2022

(54) LAPAROSCOPIC SURGICAL INSTRUMENT

(71) Applicant: Lapovations, LLC, Fayetteville, AR (US)

(72) Inventors: Chris Taylor, Harrison, AR (US); Jared Greer, Fayetteville, AR (US); Terry Oquin, Fairhope, AL (US); Byron Smith, Nashville, TN (US)

(73) Assignee: Lapovations, LLC, Fayetteville, AR (US)

(*) Notice: Subject to any disclaimer, the term of this patent is extended or adjusted under 35 U.S.C. 154(b) by 0 days.

(21) Appl. No.: 16/041,528

(22) Filed: Jul. 20, 2018

(65) Prior Publication Data

US 2019/0175164 A1 Jun. 13, 2019

Related U.S. Application Data

(60) Provisional application No. 62/597,141, filed on Dec. 11, 2017.

(51) Int. Cl.
*A61B 17/02* (2006.01)
*A61B 17/34* (2006.01)
(Continued)

(52) U.S. Cl.
CPC ...... *A61B 17/0281* (2013.01); *A61B 17/3403* (2013.01); *A61B 17/3415* (2013.01);
(Continued)

(58) Field of Classification Search
CPC . F16B 47/00; A61B 17/0281; A61B 17/3403; A61B 17/3415; A61B 2017/3407; A61B 2017/3419; A61B 17/442
See application file for complete search history.

(56) References Cited

U.S. PATENT DOCUMENTS 3,794,044 A * 2/1974 Vennard ............... A61B 17/442
606/123
4,892,517 A 1/1990 Yuan
(Continued)

FOREIGN PATENT DOCUMENTS

CN 202960684 U 6/2013
CN 203953814 U 11/2014
(Continued)

OTHER PUBLICATIONS

Böhm, B., M. Knigge, M. Kraft, K. Gründel, and U. Boenick. "Influence of Different Trocar Tips on Abdominal Wall Penetration during Laparoscopy." Surgical Endoscopy 12, No. 12 (Jun. 30, 1998): 1434-438. doi: 10.1007/s004649900876.
(Continued)

*Primary Examiner* — Kevin T Truong
*Assistant Examiner* — Tracy L Kamikawa
(74) *Attorney, Agent, or Firm* — Waller Lansden Dortch & Davis, LLP; Matthew C. Cox

(57) ABSTRACT

A surgical device that provides a suction force against a patient's body. The device includes a stem having a proximate end and a distal end, the stem disposed about a channel, a suction head extending from the stem and defining a suction chamber in fluid communication with the channel, the suction head having a contact surface, and an articulating joint disposed between the contact surface of the suction head and the distal end of the stem. The articulating joint may be an annular joint and a living hinge. The surgical device may also include a handle disposed about the channel directly or may be disposed about the stem which is disposed about the channel. The handle may include a plurality of ribs extending outward which form a profile matching a profile of a user's hand.

18 Claims, 26 Drawing Sheets

(51) Int. Cl.
F16B 47/00 (2006.01)
A61B 17/30 (2006.01)
(52) U.S. Cl.
CPC ..... *A61B 17/3474* (2013.01); *A61B 2017/306* (2013.01); *F16B 47/00* (2013.01)

(56) References Cited

U.S. PATENT DOCUMENTS

| | | | |
|---|---|---|---|
| 5,019,086 A * | 5/1991 | Neward | A61B 17/442 606/123 |
| 5,224,947 A | 7/1993 | Cooper et al. | |
| 5,281,229 A | 1/1994 | Neward | |
| 5,336,158 A | 8/1994 | Huggins | |
| 5,353,785 A | 10/1994 | Wilk | |
| 5,395,379 A | 3/1995 | Deutchman | |
| 5,545,123 A | 8/1996 | Ortiz et al. | |
| 5,810,840 A * | 9/1998 | Lindsay | A61B 17/442 606/122 |
| 5,865,730 A | 2/1999 | Fox et al. | |
| 5,865,827 A * | 2/1999 | Bullister | A61B 17/30 248/362 |
| 5,935,136 A * | 8/1999 | Hulse | A61B 17/442 606/119 |
| 6,042,539 A | 3/2000 | Harper et al. | |
| 6,059,795 A | 5/2000 | Wallace et al. | |
| 6,074,399 A * | 6/2000 | Wallace | A61B 17/442 606/122 |
| 6,179,845 B1 * | 1/2001 | Peters | A61B 17/442 604/74 |
| 6,355,047 B1 | 3/2002 | Wallace et al. | |
| 7,234,743 B2 | 6/2007 | Robinson | |
| 7,585,281 B2 | 9/2009 | Nezhat et al. | |
| 7,992,908 B2 | 8/2011 | Finck | |
| 9,050,133 B1 | 6/2015 | Boone, III et al. | |
| 9,408,633 B2 * | 8/2016 | Leitch | A61B 17/42 |
| 2005/0010197 A1 | 1/2005 | Lau et al. | |
| 2005/0203334 A1 | 9/2005 | Lonky et al. | |
| 2006/0229671 A1 * | 10/2006 | Steiner | A61B 17/0401 606/232 |
| 2007/0270745 A1 | 11/2007 | Nezhat et al. | |
| 2008/0058851 A1 | 3/2008 | Edelstein et al. | |
| 2008/0125792 A1 * | 5/2008 | Giardina | A61B 17/442 606/123 |
| 2010/0249755 A1 | 9/2010 | Zappala | |
| 2013/0197315 A1 | 8/2013 | Foley | |
| 2013/0296751 A1 * | 11/2013 | Martin | A61H 21/00 601/148 |
| 2013/0304081 A1 * | 11/2013 | George | A61B 17/442 606/123 |
| 2015/0272314 A1 * | 10/2015 | Vandenbroucke | B25G 3/36 401/268 |
| 2017/0071323 A1 * | 3/2017 | Yang | A46B 15/0055 |
| 2017/0333643 A1 | 11/2017 | Taylor et al. | |

FOREIGN PATENT DOCUMENTS

| | | |
|---|---|---|
| CN | 203988534 U | 12/2014 |
| CN | 107335103 A | 11/2017 |
| WO | 02088546 A1 | 11/2002 |
| WO | 2014125434 A1 | 8/2014 |

OTHER PUBLICATIONS

Corson, Stephen L., MD, Frances R. Batzer, MD, Benjamin Gocial, MD, and Greg Maislin, MS. "Measurement of the Force Necessary for Laparoscopic Trocar Entry." The Journal of Reproductive Medicine 34, No. 4 (Apr. 1989): 282-84.

Fuller, Janie, DDS, Walter Scott, Ph.D., Binita Ashar, MD, and Julia Corrado, MD. "Laparoscopic Trocar Injuries: A Report from a U.S. Food and Drug Administration (FDA) Center for Devices and Radiological Health (CDRH) Systematic Technology Assessment of Medical Products (STAMP) Committee: FDA Safety Communication." U.S. Food and Drug Administration. Nov. 7, 2003. http://www.fda.gov/MedicalDevices/Safety/AlertsandNotices/ucm197339.htm.

Inan, A., M. Sen, C. Dener, and M. Bozer. "Comparison of Direct Trocar and Veress Needle Insertion in the Performance of Pneumoperitoneum in Laparoscopic Cholecystectomy." Acta Chirurgica Belgica 105, No. 5 (2005): 515-18. doi: 10.1080/00015458.2005.11679771.

La Chapelle, Claire F., Willem A. Bemelman, Bart MP Rademaker, Teus A. Van Barneveld, and Frank W. Jansen. "A Multidisciplinary Evidence-based Guideline for Minimally Invasive Surgery." Journal of Gynecological Surgery 9 (Jan. 24, 2012): 271-82. doi:10.1007/s10397-012-0731-y.

Toro, Adriana, Maurizio Mannino, Giovanni Cappello, Andrea Di Stefano, and Isidoro Di Carlo. "Comparison of Two Entry Methods for Laparoscopic Port Entry: Technical Point of View." Diagnostic and Therapeutic Endoscopy 2012 (Apr. 5, 2012): 1-7. doi:10.1155/2012/305428.

Vilos, George A., MD, Artin Ternamian, MD, Jeffrey Dempster, MD, and Philippe Y. Laberge, MD. "Laparoscopic Entry: A Review of Techniques, Technologies, and Complications." Journal of Obstetrics and Gynaecology Canada 193 (May 2007): 433-47; http://sogc.org/wp-content/uploads/2013/01/gui193ECPG0705wDisclaimer.pdf.

Lapdome By Dome; Laparoscopic Surgery, Laparoscopic Market Dynamics; domemedical.com/laparoscopic-surgery/ (accessed Jul. 2016), four pages.

strategyr.com/pressMCP-6143.asp (accessed Jul. 2016).

Laparoscopic Devices Market—Global Industry Analysis, Size and Forecast, 2015-2025; http://www.futuremarketinsights.com/reports/laparoscopic-devices-market (accessed Jul. 2016), four pages.

Springer-Verlag, 2017 Springer International Publishing AG. Part of Springer Nature, Vacuum-assisted abdominal wall lift for minimal-access surgery: a porcine model study; https://link.springer.com/article/10.1007/s00464-004-2131-5, six pages.

Rhodes, Ronald A., "Laparoscopic Trocar Complications". The 3rd Edition: Prevention & Management, http://laparoscopy.blogs.com/prevention_management_3/2010/11/laparoscopic-trocar-complications.html; nine pages.

International Search Report and Written Opinion for PCT/US2017/033887, dated Aug. 15, 2017, 14 pages.

PCT/US2018/065014 International Search Report and Written Opinion, dated Mar. 28, 2019, 13 pages.

* cited by examiner

LAPAROSCOPIC SURGICAL INSTRUMENT

CROSS-REFERENCES TO RELATED APPLICATIONS

This application claims priority to and benefit of U.S. Provisional Patent Application No. 62/597,141 entitled "Laparoscopic Surgical Instrument" which is hereby incorporated by reference in its entirety.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present disclosure relates generally to surgical devices. More particularly, embodiments of the subject matter described herein relate to a device and methods for lifting tissue of a patient, including lifting tissue prior to insertion of a surgical instrument such as a trocar or Veress needle.

During various surgical procedures, including laparoscopy, surgical instruments such as a trocar, Veress needle, or access port may be inserted into the tissue of a human or animal. In some procedures, the instrument is inserted in a position to access the abdominal cavity. The initial surgical instrument or trocar is preferably placed through the umbilicus because the abdominal wall is at its thinnest in this region. A laparoscopic camera is then placed through this initial trocar to aid in visualizing the intraabdominal cavity and the structures therein. Carbon dioxide gas is then used to insufflate the abdominal cavity, thereby creating a pneumoperitoneum or space to operate. Once the pneumoperitoneum is created, secondary trocars can be placed under direct visualization utilizing the laparoscopic camera thus reducing the risk of injury.

Patient injuries most often occur during initial placement of the trocar or Veress needle, which is generally considered to be the most dangerous portion of a laparoscopic surgery. Currently, there are two common methods for the placement of the primary umbilical trocar: the closed insertion technique and the open insertion (Hasson) technique.

The closed insertion technique can be accomplished either before or after the creation of the pneumoperitoneum. Some surgeons prefer insufflating the abdominal cavity prior to the placement of the initial trocar. This is accomplished with the use of a Veress needle. The needle is blindly introduced through an umbilical incision. Carbon dioxide gas is introduced through the Veress needle, elevating the abdominal wall away from the underlying structures. The Veress needle is then removed, and the primary trocar placed.

Other surgeons prefer placing the primary trocar prior to insufflating the abdomen. This is the direct entry method and is performed using a technique called a "controlled jab." The trocar is placed through an umbilical incision under controlled force using a stabbing motion with care not to penetrate beyond the abdominal wall. Most surgeons elevate the abdominal wall during closed insertion of either the primary trocar or the Veress needle. This reduces the risk of injury to underlying structures.

The most common type of injury is to vascular structures, bowel, or to other visceral organs. Multiple studies have shown that complication rates are similar between the Veress needle and direct entry as well as between the closed insertion technique and the open insertion (Hasson) technique. Various techniques and inventions have been described to assist with elevation of the abdominal wall to facilitate closed insertion trocar or Veress needle placement. This includes rarely used devices such as retractors and lifting rods used to mechanically elevate the abdominal wall thereby creating negative pressure within the abdomen allowing a space for initial trocar placement or room to operate without the need for creating a pneumoperitoneum.

More commonly, two conventional manual techniques for lifting the abdominal wall are utilized. The first method involves grasping and lifting the abdominal wall below or on either side of the umbilicus with one's hand. The second method utilizes perforating towel clips placed in a similar location to provide a handle on which to lift and elevate the abdominal wall. Each of these techniques require that sufficient elevation of the abdominal wall is maintained in opposition to the downward force generated during primary trocar or Veress needle placement. Although providing a more secure grasp of the abdominal wall, towel clips pierce the abdominal skin and therefore risk injury and trauma to vessels and tissue. This is also a source of postoperative discomfort to what is intended to be a minimally invasive procedure. Grasping and lifting the abdominal wall by hand poses its own challenges. Whether the surgeon is lifting the abdomen below the umbilicus or the surgeon and his assistant are lifting on either side of the umbilicus, it can be difficult to maintain a grip and the proper elevation to ensure inadvertent injury does not occur to the underlying structures. The shape, elasticity, and overall thickness of the abdominal wall can also prohibit one from adequately grasping the abdomen by hand. Also, lifting the full thickness of the abdominal wall by hand risks inadvertently grasping and elevating the omentum and other underlying structures together with the abdominal wall bringing these structures into the path of the trocar or Veress needle.

In an effort to improve on current tools and techniques, a number of devices have been developed. One recent apparatus, marketed under the name of LapDome by DOME Medical Technologies, Inc., utilizes a dome shaped device and negative pressure generated from external operating room suction to raise the abdominal wall within the dome thereby creating intraabdominal space. A Veress needle is then introduced through the dome and into the elevated abdominal cavity. The abdominal cavity is then insufflated with carbon dioxide gas, and the surgery can commence as usual.

There are several drawbacks to using the LapDome and similar devices. First, it is a bulky apparatus fixated over the abdomen and umbilicus. Second, the LapDome can be used only with the Veress needle technique and therefore limits a surgeon to a technique that he or she may not be comfortable with performing.

What is needed then are improvements to devices and methods for laparoscopic surgery, and particularly for manipulating and lifting patient tissue for insertion and placement of a surgical device during a surgical procedure, such as but not limited to a trocar or Veress needle.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of some embodiments of the present disclosure is a surgical device including a handle, a stem coupled to the handle, and a suction head coupled to the stem. A valve is disposed on the suction head. Suction tubing may be in fluid communication with the valve, which is in fluid communication with a suction chamber of the suction head, thereby creating a suction force between the suction head and the skin of a patient. Once a suction force is established between the suction head and the patient, the user may then lift the surgical device away from the patient's body to lift tissue for trocar insertion.

Another aspect of some embodiments of the present disclosure provides a handle, a stem coupled to the handle, and a suction head coupled to the stem. A valve is disposed on the stem. Another embodiment of the present disclosure includes the valve disposed on the handle.

A further aspect of some embodiments of the present disclosure provides a surgical device including a handle and a suction head, wherein a negative pressure suction force may be easily released by manual operation of a pressure release on the suction head.

Another aspect of some embodiments of the present disclosure is to provide a device and associated methods to lift tissue prior to trocar or Veress needle insertion to allow surgeons to utilize either trocar insertion method.

A further aspect of some embodiments of the present disclosure is a surgical device that can include a stem defining a channel, the stem having a distal end and a proximate end, a suction head extending from the proximate end of the stem and defining a suction chamber in fluid communication with the channel, the suction head having a contact surface, and an articulating joint disposed between the contact surface of the suction head and the distal end of the stem. Some embodiments provide that the articulating joint includes a living hinge.

Another aspect of some embodiments of the present disclosure provides surgical device that may have a stem defining a channel, the stem having a distal end and a proximate end, a suction head extending from the proximate end of the stem and defining a suction chamber in fluid communication with the channel, the suction head having a contact surface, and a handle disposed about the stem, wherein the handle may comprise a plurality of spaced ribs extending from the stem.

A further aspect of some embodiments of the present disclosure may provide a surgical device which can engage patient tissue via negative pressure from a negative pressure source. The surgical device may include a suction head defining a suction chamber, the suction head having a contact surface for engaging the patient tissue, an articulating joint extending from the suction head, and a stem extending from the articulating joint, the stem defining a channel configured to be in fluid communication with a negative pressure source, wherein the articulating joint is a living hinge.

Numerous other objects, advantages, and features of the present disclosure will be readily apparent to those of skill in the art upon a review of the following drawings and description of a preferred embodiment.

DETAILED DESCRIPTION

Figure 1:
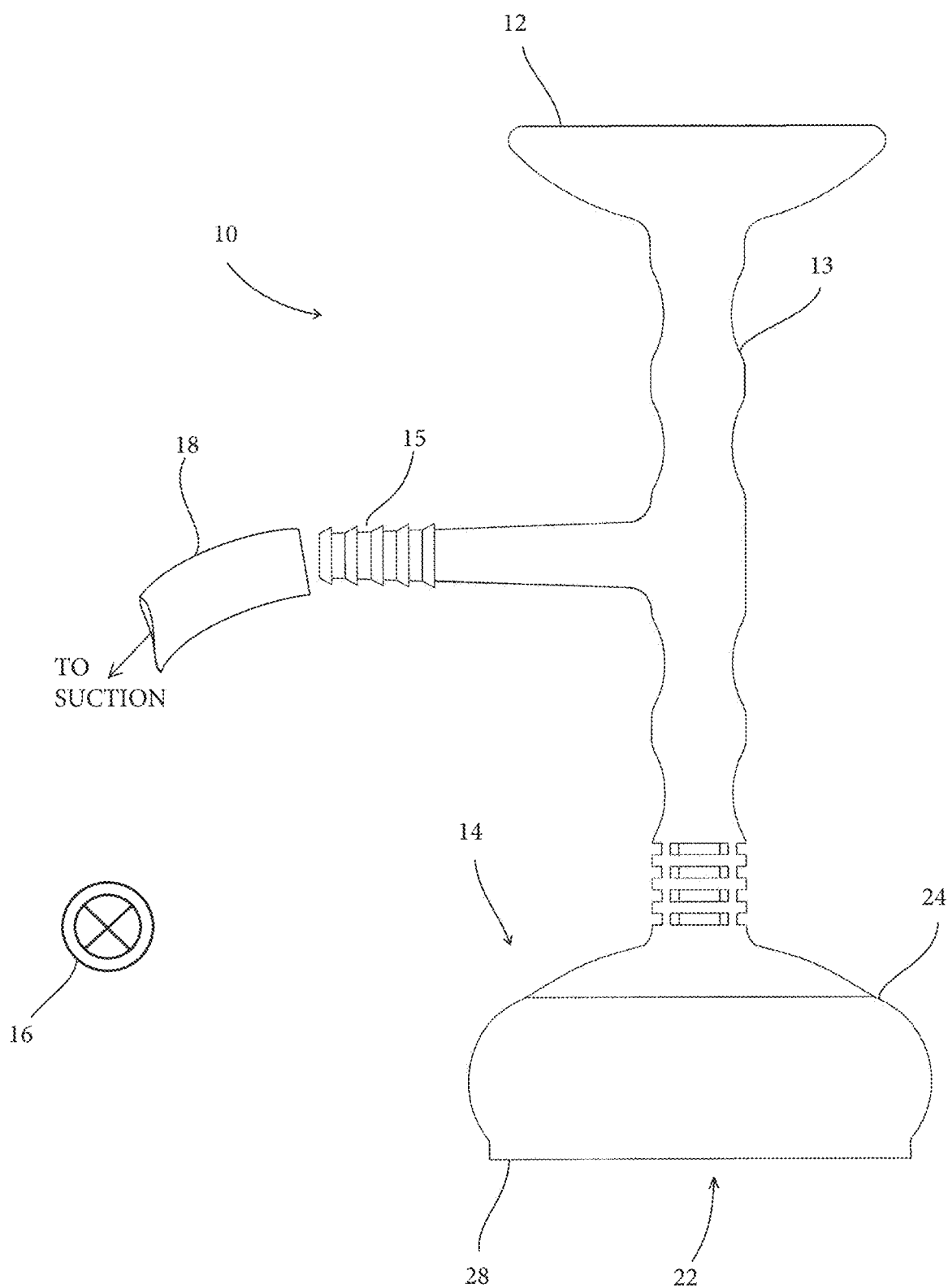
FIG. 1 is a perspective view of an embodiment of a surgical device having a channel disposed in a stem of the surgical device, a handle, and a suction head, the channel exiting the stem perpendicularly from the stem.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not limit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing. A person of skill in the art will recognize that the apparatus can assume different orientations when in use.

Figure 2:
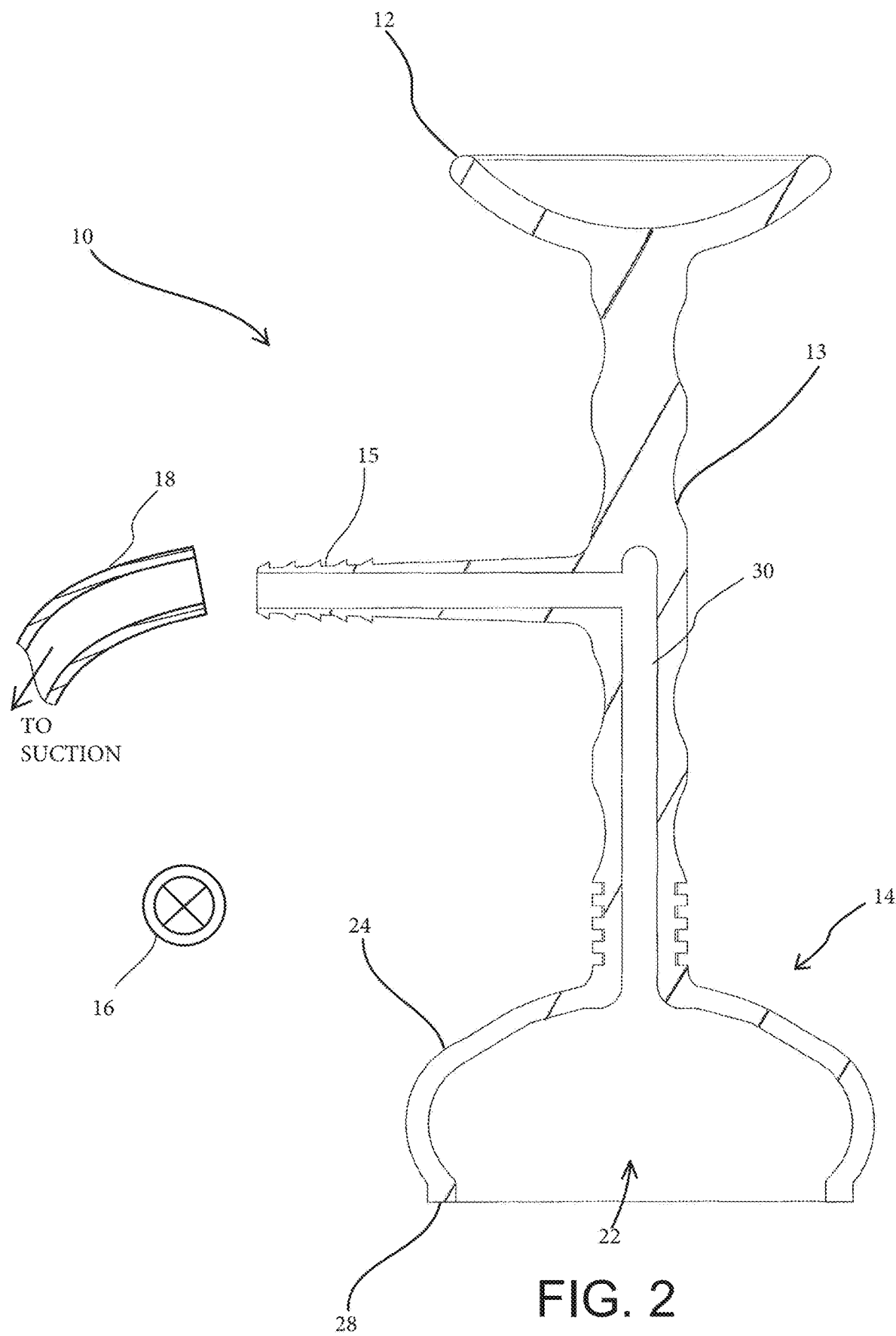
FIG. 2 is a sectional view of an embodiment of a surgical device having a channel disposed in a stem of the surgical device, a handle, and a suction head, the channel exiting the stem perpendicularly from the stem.

Referring to FIGS. 1 and 2, an embodiment of a surgical device is shown in a perspective view. Device 10 includes a handle 12, a stem 13 coupled to the handle 12, and a suction head 14 coupled to the stem 13. The suction head 14 may include a suction chamber 22 in an interior portion of the suction head 14. Suction tubing 18 is coupled to a source having negative pressure, thus providing suction to the suction tubing 18. A valve 16 may be disposed on the suction tubing 18, at the negative pressure source, or on a wall of the surgical suite. The valve 16 is operable to permit fluid communication between the suction head 14 and negative pressure source via the suction tubing 18 when suction tubing 18 is coupled to suction head 14 of the device 10. When the suction tubing 18 is coupled to the suction head 14 of the device 10 and the valve 16 is configured in an open position, air is drawn from the suction chamber 22 and through the suction tubing 18.

During use, a user may grasp handle 12 while suction head 14 engages a patient's body. Suction head 14 includes a suction cup 24 having an open suction chamber 22. A rim or contact surface 28 disposed on the suction head 14 is positioned to engage a patient's body. When contact surface 28 is positioned against a patient's body and the source having negative pressure is in fluid communication with the suction head 14 via the suction tubing 18 and valve 16, a negative pressure is drawn between the suction head 14 and the patient's body. The contact surface 28 operates as a seal between the patient's skin and the suction head 14. Once a negative pressure suction force is established between the device 10 and the patient via the suction head 14, the user may then use handle 12 to manually lift the patient's tissue while maintaining a negative pressure seal between the patient's body and the contact surface 28. When the proper negative suction force has been achieved, a user may close the valve 16 such that negative pressure source and the suction head 14 are no longer in fluid communication. Once tissue is lifted, the user may then insert a trocar or Veress needle using any suitable insertion technique.

In some embodiments, the various components may be integrated into a single piece, as shown in FIG. 2, whereas other embodiments have each piece being formed separately and subsequently assembled. When the device 10 is one integral piece, the device may be formed or molded out of a single material. In other embodiments, the device 10 may be formed of separate parts and materials, for example the device 10 may be overmolded with a second material such as silicone. Any combination of formed or integrated parts may be implemented as known by one of skill in the art.

Other embodiments of the device may include a valve 16 positioned at or on the device 10, thus permitting a user to control fluid communication between the suction chamber 22 of the device 10 and a negative pressure source. For example, once the need for lifting the patient's tissue has terminated, the negative pressure suction force may be released by disconnecting the suction tubing 18 from a valve 16 positioned on the device 10 and configuring the valve 16 in an open configuration. The opening of the valve 16 releases the negative pressure seal between the patient's body and the suction head 14. Various valves 16 may be implemented for use, including a stopcock, a medical check valve, a quarter turn valve, or any other valve that a person of skill in the art will recognize as suitable for the intended purpose.

The valve 16 may be placed in an open configuration and a closed configuration. The open configuration allows air to pass through the valve 16, and the closed configuration prevents air from passing through the valve 16. The valve 16 may be coupled to a variety of sources such as a negative pressure source. The valve 16 may also be exposed to ambient air.

Various connectors may be implemented in the various embodiments of the device 10. FIG. 1 demonstrates one fitting 15 which may be implemented for connecting a suction tube 18 to a device 10. Other fittings 15 may be implemented in each embodiment and one of ordinary skill in the art would recognize the various appropriate connectors which could be implemented with the device 10.

Figure 3:
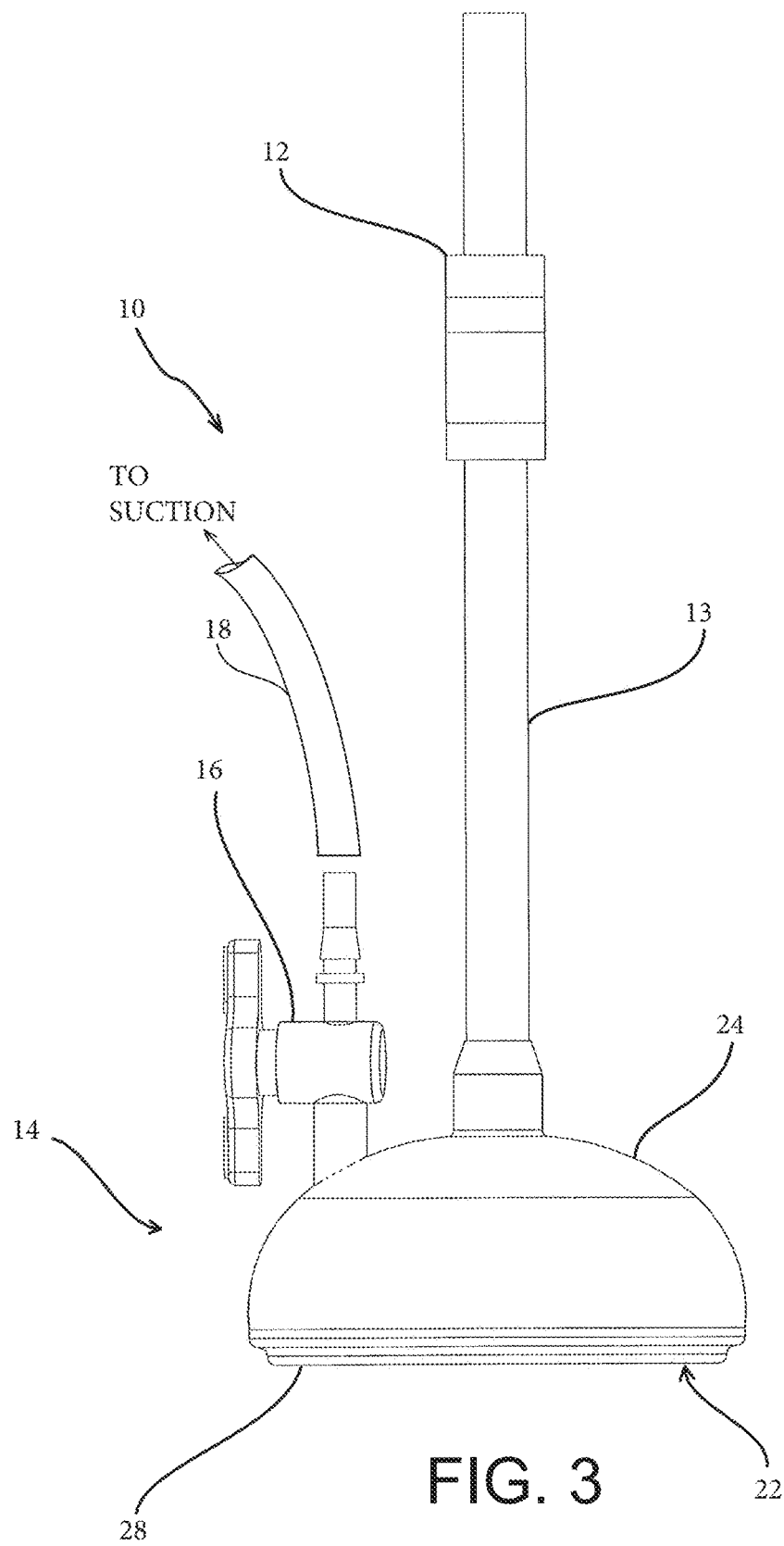
FIG. 3 is a perspective view of an embodiment of a surgical device having a stopcock valve disposed on a suction head of the surgical device, a stem, and a handle.
Figure 4:
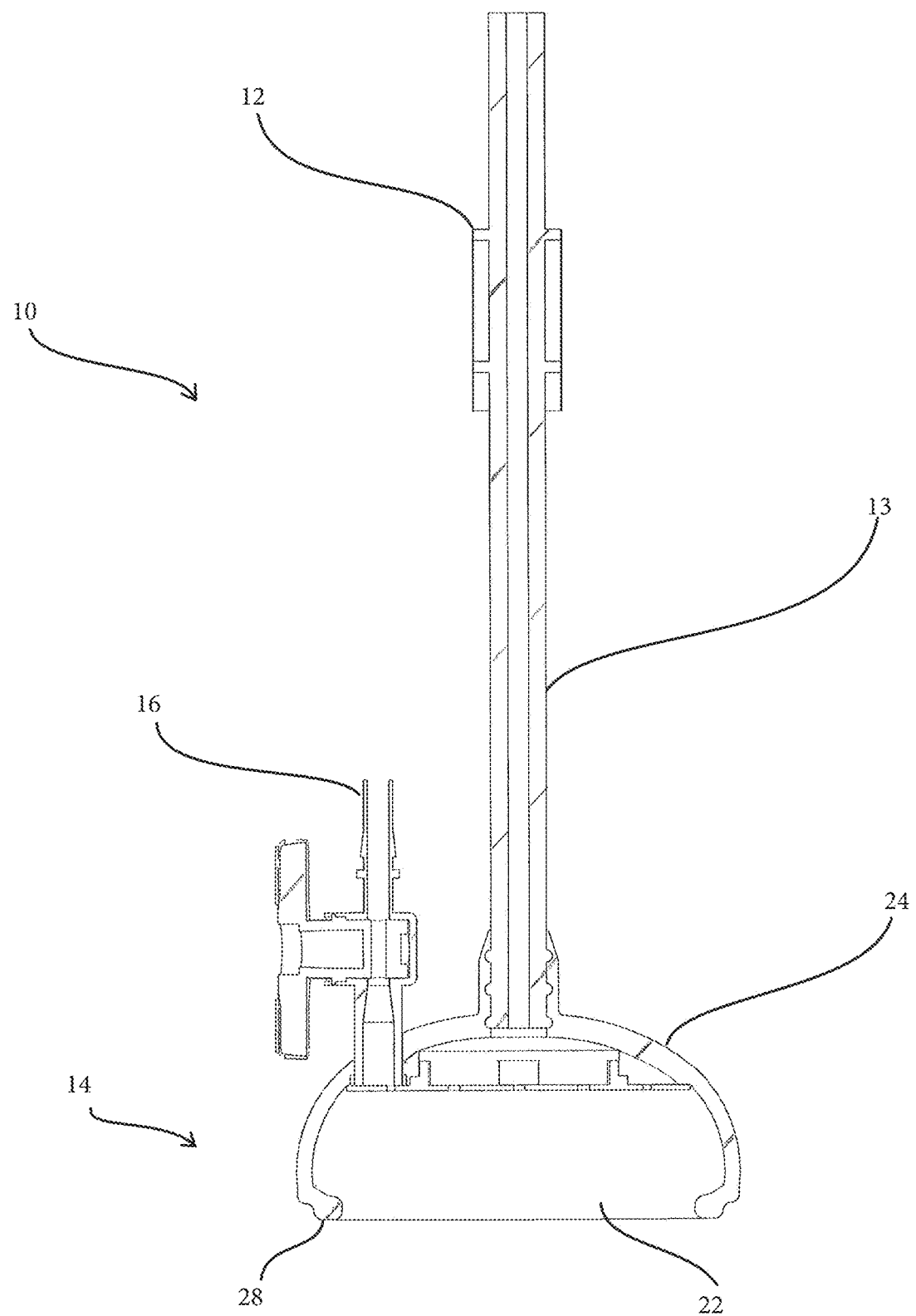
FIG. 4 is a sectional view of an embodiment of a surgical device having a stopcock valve disposed on a suction head of the surgical device, a stem, and a handle.

FIGS. 3 and 4 provides an illustration of a surgical device 10 having a valve 16 positioned on the suction head 14. The valve 16 allows fluid communication across the suction head 14 when the valve is in an open configuration such that air may be transferred directly across the suction head 14 from the interior of the suction head 14 to the suction tubing 18 or from the ambient air to the interior of the suction head 14. In this embodiment, suction tubing 18 is coupled directly to the device 10 and the airflow is controlled by the valve 16. Alternative embodiments may include a port in the suction head 14 which provides a surface to which a valve 16 may detachably couple to the suction head 14. In this embodiment, a user may select the type of valve to be used in providing fluid communication between the source having negative pressure and the suction head 14. For example, a user may optionally select in one procedure to detachably couple a stopcock valve to the suction head 14 and in a second procedure a quarter turn valve having a secondary attachment for a second device requiring suction from a source having negative pressure. One of skill in the art would recognize a variety of couplings for detachably coupling a valve 16 to a suction head 14, including barbed connectors, bayonet connectors, compression fittings, threaded connectors, bores, luer locks, pipe thread connectors, panel mounts, quick disconnect couplings, etc.

Figure 5:
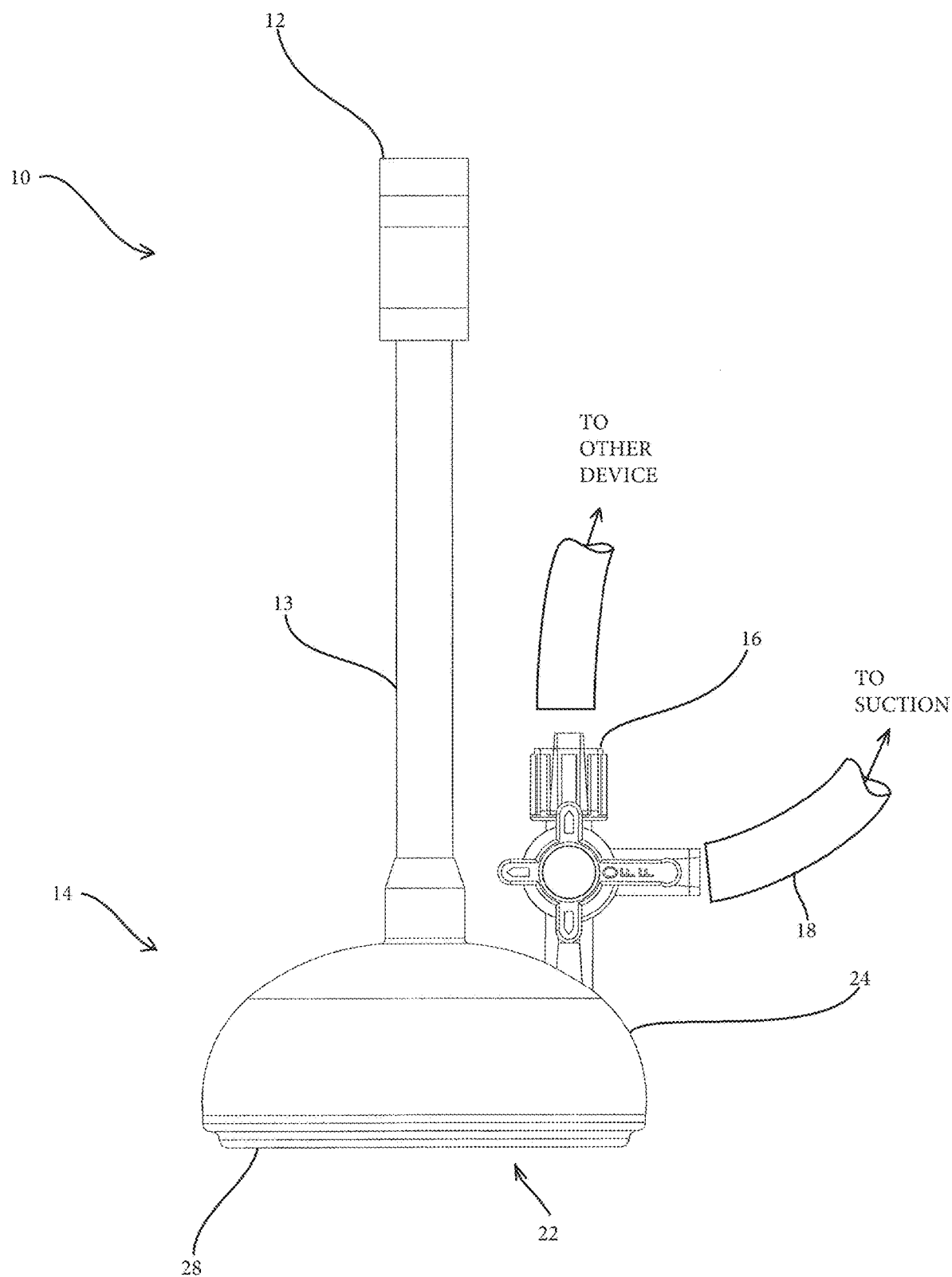
FIG. 5 is a perspective view of an embodiment of a surgical device having a valve disposed on a suction head of the surgical device, a stem, and a handle, the valve operable to interconnect other devices, the valve configured to permit fluid communication between a negative pressure source, a suction chamber of the device, and a second device.
Figure 6:
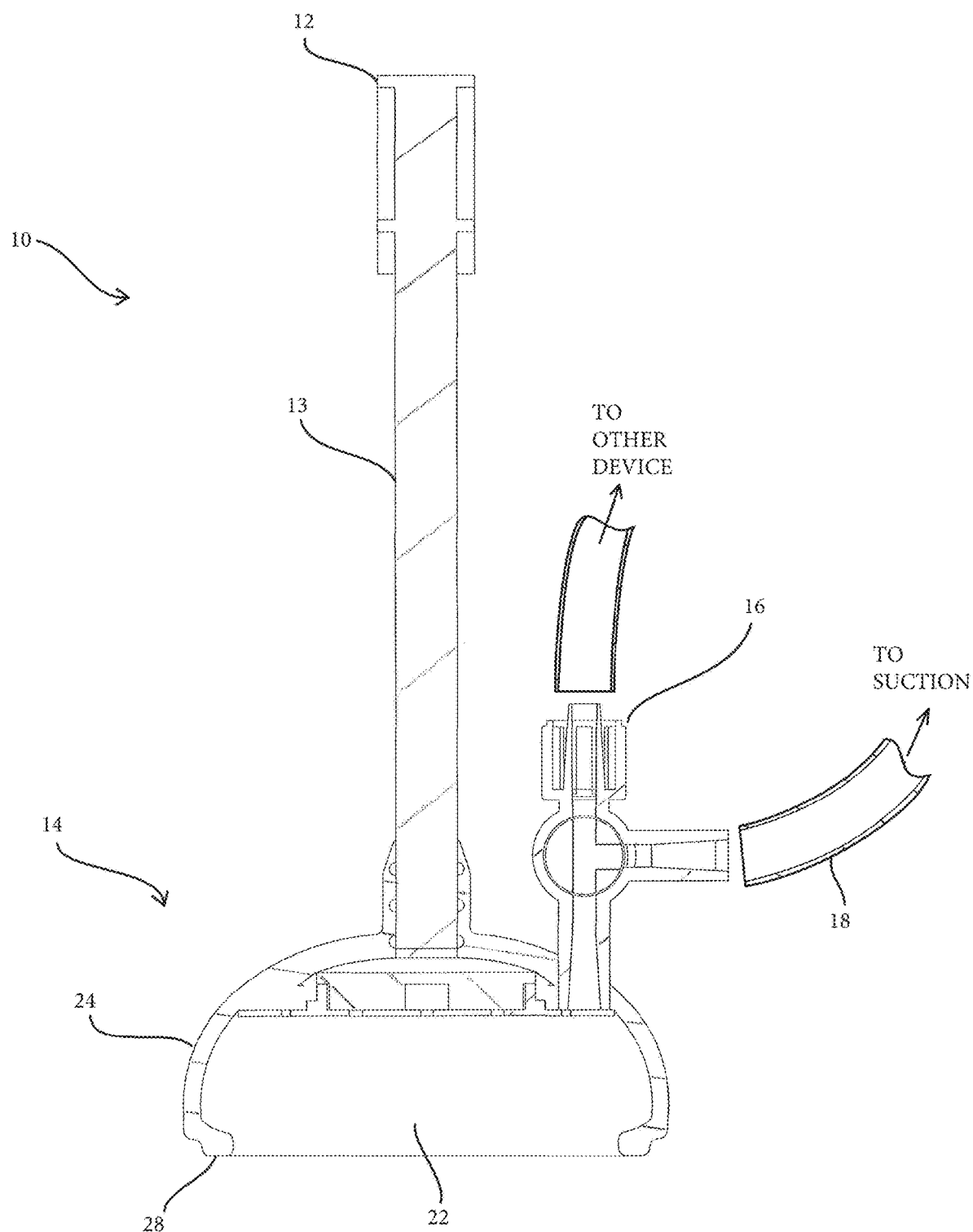
FIG. 6 is a sectional view of an embodiment of a surgical device having a valve disposed on a suction head of the surgical device, a stem, and a handle, the valve operable to interconnect with other devices, the valve configured to permit fluid communication between a negative pressure source, a suction chamber of the device, and a second device.
Figure 7:
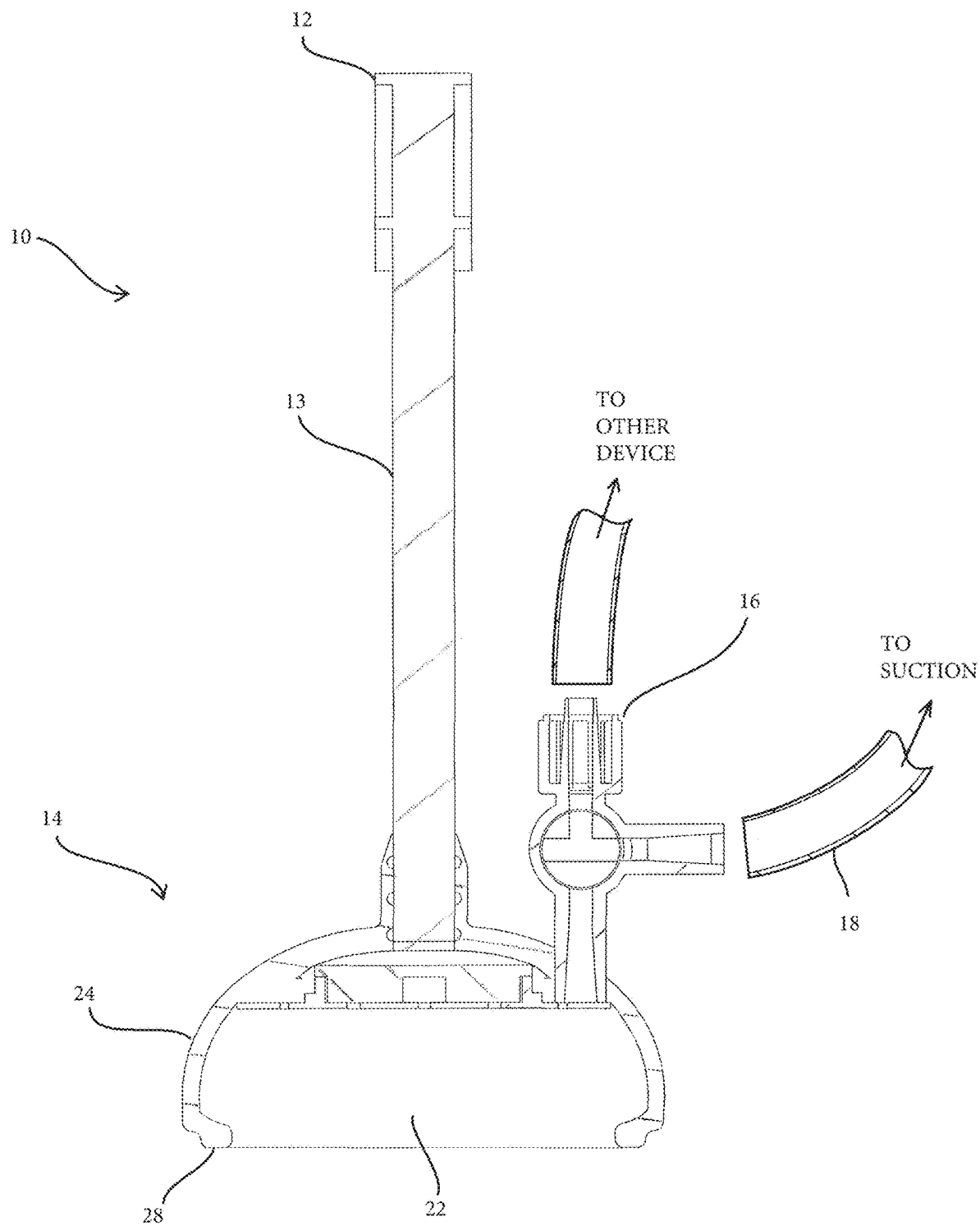
FIG. 7 is a sectional view of an embodiment of a surgical device having a valve disposed on a suction head of the surgical device, a stem, and a handle, the valve operable to interconnect with other devices, the valve configured to prevent fluid communication between a negative pressure source and a second device.

FIGS. 5-7 portray one embodiment in which the surgical device 10 has a valve 16 positioned directly on the suction head 14, and the valve is operable to allow daisy chaining or interconnection of multiple devices requiring access to a negative pressure source. This allows the surgical device 10 to be used in series or in parallel (depending on the valve implemented) with any other device requiring access to a source of negative pressure. Thus, multiple lines from the source of negative pressure are not required and simplifies the surgical field from excessive clutter if multiple tools requiring a negative pressure source are being used.

To interconnect multiple devices requiring access to a source of negative pressure, the device 10 may implement a three-way valve 16, as shown in FIGS. 5-7. FIG. 6 demonstrates one embodiment in which the three-way valve 16 is positioned such that the suction chamber 22 of the suction head 14, a second device, and a source of negative pressure are all in fluid communication via the three-way valve 16. FIG. 7 demonstrates another embodiment in which the three-way valve 16 is positioned such that the suction chamber 22 is not in fluid communication with the source of negative pressure. As is shown, the second device may still be in fluid communication with the source of negative pressure even when the valve 16 is preventing fluid communication between the suction chamber 22 and the source of negative pressure.

In one embodiment, the device 10 may include a stem 13 that is rigid. The rigid stem extends from the handle 12. The rigid stem 10 provides a rigid support from the handle 12 to the suction head 14. Thus, when the suction head 14 is in a negative pressure seal with the patient's tissue and a user is manipulating a patient's tissue in a procedure or operation, the suction head 14 follows the movement of the handle substantially proportionally, thus allowing the user a high level of control over the device 10 and the patient's tissue under the negative pressure seal with the device 10.

In other embodiments, the device 10 may include a flexible stem 13. The flexible stem 13 extends from the handle 12. The flexible stem 10 provides a flexible support from the handle 12 to the suction head 14. Thus, when a user is manipulating a patient's tissue in a procedure or operation, the suction head 14 may be manipulated from positions that have a constrained space. The flexible stem 13 may also allow the suction head 14 to maintain optimal contact with the patient's tissue during manipulation as the flexible stem will flex and bend under torque, thus eliminating or minimizing the torque at the contact surface 28 between the suction head 14 and the patient's tissue. This may help prevent a disruption of the negative pressure seal between the patient and the device 10. The flexible stem 13 may be operable to allow varying levels of flex in the stem 13. In certain procedures, it may be beneficial to implement a stem 13 having maximum flex to allow the suction head 14 to maintain optimal contact with the patient's tissue as described above. In this implementation, minimal torqueing force is imparted by the materials of the stem 13 and the tissue is translated in substantially the same direction as the direction of the force being applied by the user to the device 10. In some embodiments, the channel 30 may be reinforced to prevent collapse of the channel 30 because the flexible nature of the stem 13.

In embodiments when the manipulation of a patient's tissue may require more than translation along the direction of the applied force alone, the stem 13 may comprise a semi-flexible material, thus allowing the user to apply a torqueing force to the device 10 that is at least partially translated to the patient's tissue. In this application, the user may use a torqueing force to properly position the user's hands to prevent interference with any procedures such as trocar insertion or Veress needle insertion during a laparoscopic surgical procedure using the device 10.

The stem 13 may be formed from a variety of materials most suitable for the desired rigidity or flexibility in the stem 13. Those of ordinary skill in the art will recognize numerous materials that may be used in the construction of the stem including ABS, Acrylic, HDPE, Polyester, Nylon, PET, LDPE, PS, PP, PVC, PTFE, etc.

Figure 8:
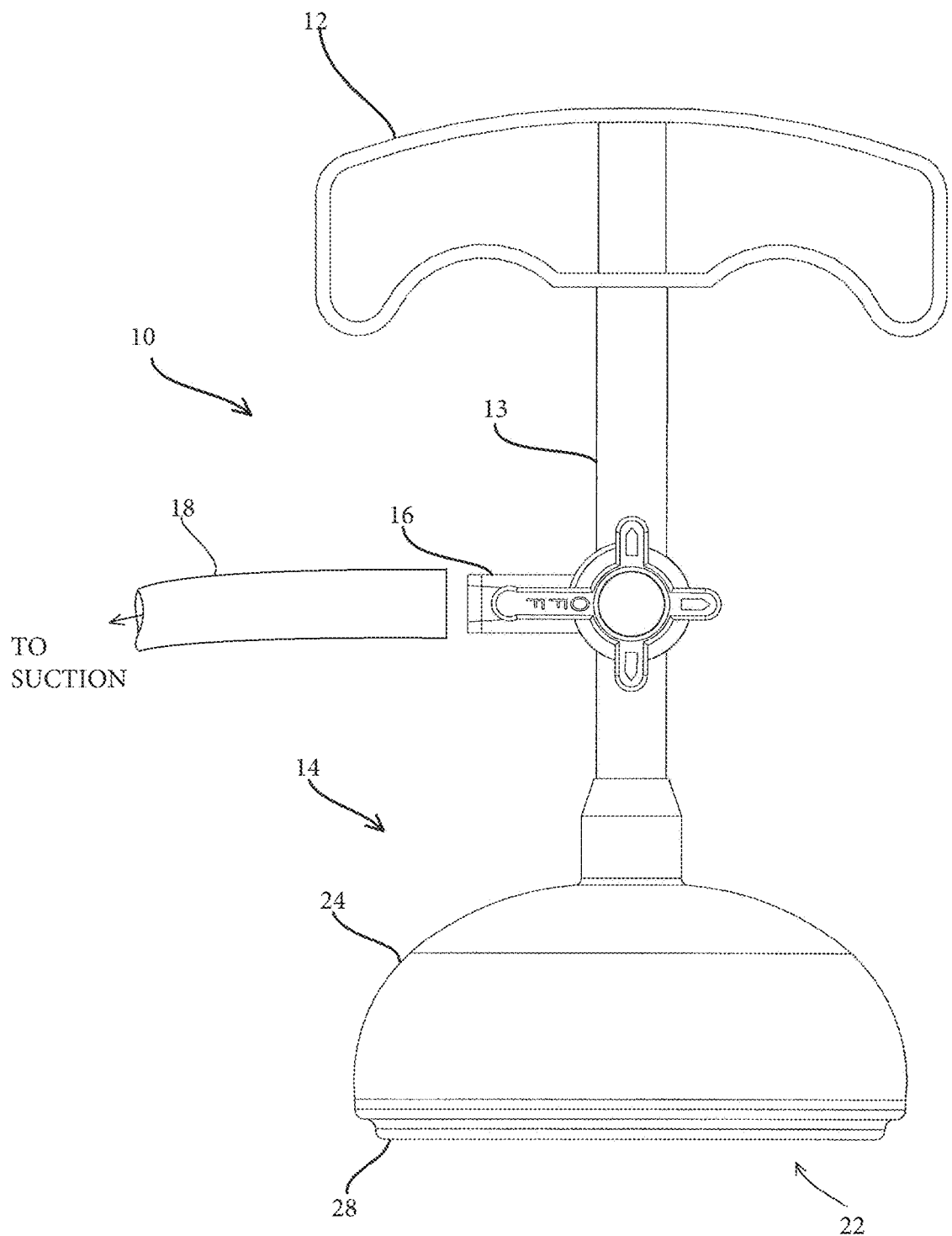
FIG. 8 is a perspective view of an embodiment of a surgical device having a valve disposed on the stem of the surgical device, a handle, and a suction head, the valve operable to allow for the removal of the negative pressure source while still maintaining the suction force between the suction head and the skin of a patient.
Figure 9:
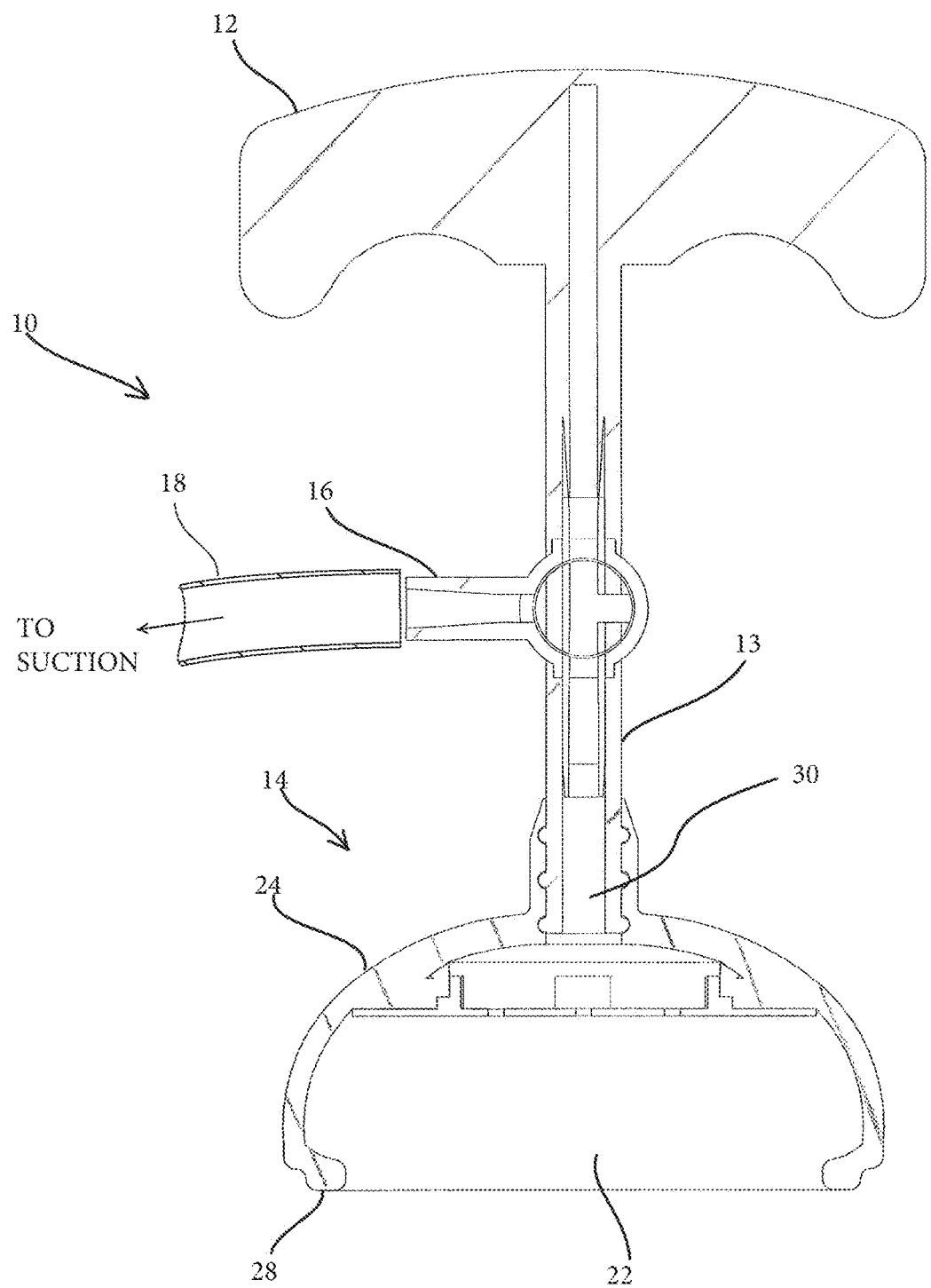
FIG. 9 is a sectional view of an embodiment of a surgical device having a valve disposed on the stem of the surgical device, a handle, and a suction head, the valve operable to allow for the removal of the negative pressure source while still maintaining the suction force between the suction head and the skin of a patient.
Figure 10:
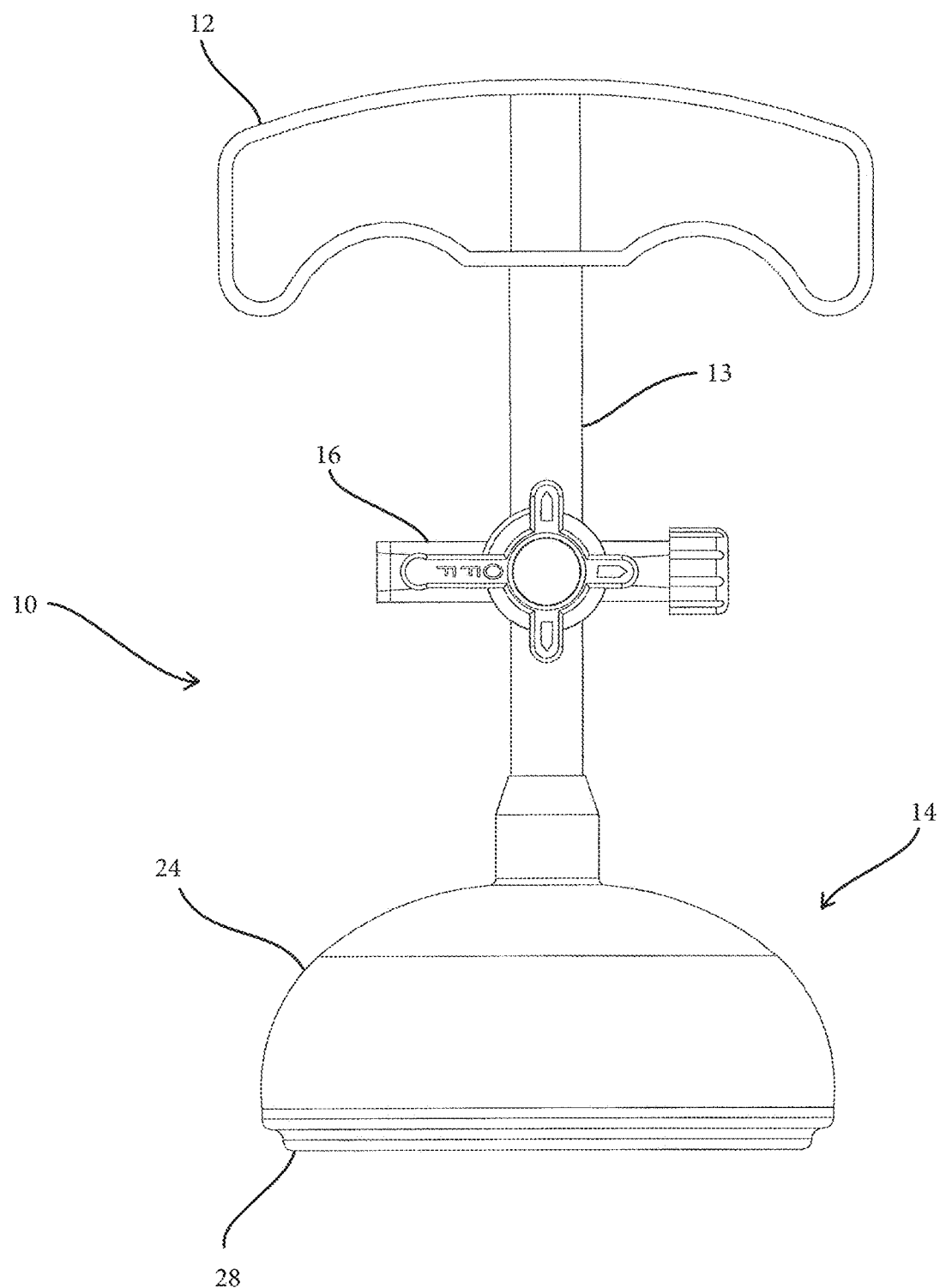
FIG. 10 is a perspective view of an embodiment of a surgical device having a valve disposed on the stem of the surgical device, a handle, and a suction head, the valve being operable to interconnect with other devices and the valve being operable to allow for the removal of the negative pressure source while still maintaining the suction force between the suction head and the skin of a patient.
Figure 11:
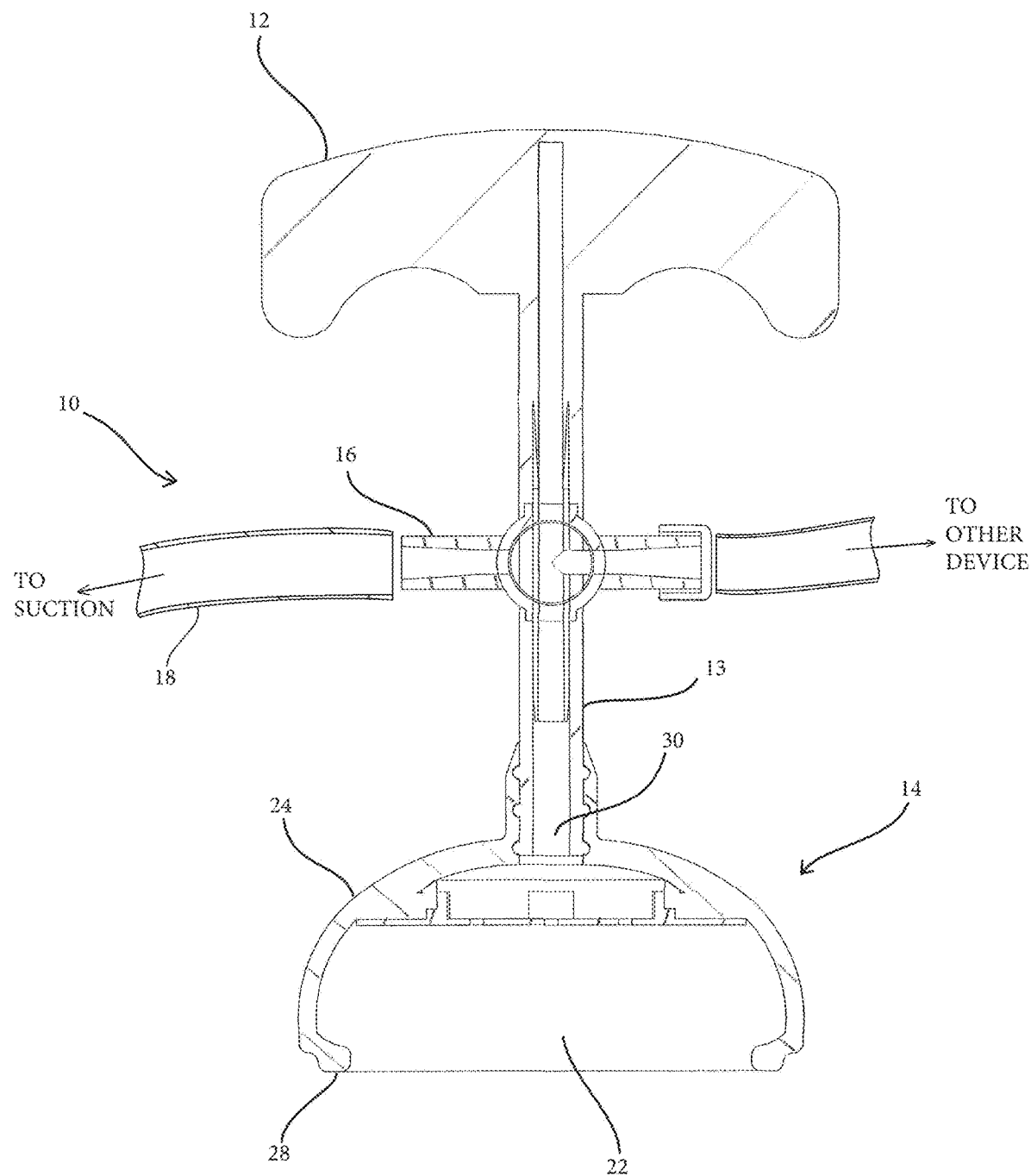
FIG. 11 is a sectional view of an embodiment of a surgical device having a valve disposed on the stem of the surgical device, a handle, and a suction head, the valve being operable to interconnect with other devices and the valve being operable to allow for the removal of the negative pressure source while still maintaining the suction force between the suction head and the skin of a patient.

FIGS. 8 and 9 portray one embodiment in which a valve 16 may be coupled to the stem 13 of the device 10. In this embodiment, the stem 13 may include a channel 30 disposed within at least a portion of the stem 13. The channel 30 may be in fluid communication with the suction head 14 and the valve 16. Thus, in this embodiment, the valve 16 is in fluid communication with the suction head 14 via the channel 30 disposed in the stem 13. The valve 16 may be operable to selectively permit fluid communication either from a negative pressure source or ambient air to the channel 30. The valve 16 may be further operable to allow for the removal of the negative pressure source or fluid communication with the negative pressure source while still maintaining the suction force between the suction head 14 and the skin of a patient FIGS. 10 and 11 depict one embodiment in which a valve 16 is coupled to the stem 13, the valve 16 operable to permit daisy-chaining or interconnection between other devices requiring access to a negative pressure source. The valve 16 may be operable to allow a user to remove the device 10 from a negative pressure source while maintaining a suction force or seal with a patient. The valve 16 may further may be operable to provide the additional ability of being able to connect to the negative pressure source and/or to multiple other devices. For example, valve 16 could couple via suction tubing to another device or to suction on a first side. A cap on a second side of the valve 16 could be removed to allow for fluid communication between the device 10 and a negative pressure source and/or another device. A person of skill in the art will recognize that the apparatus may implement a variety of valves 16 in each embodiment, each valve 16 providing varying benefits including daisy-chaining, low-profile, selective fluid communication to a variety of sources including the negative pressure source or ambient air, pressure gauges, etc.

Figure 12:
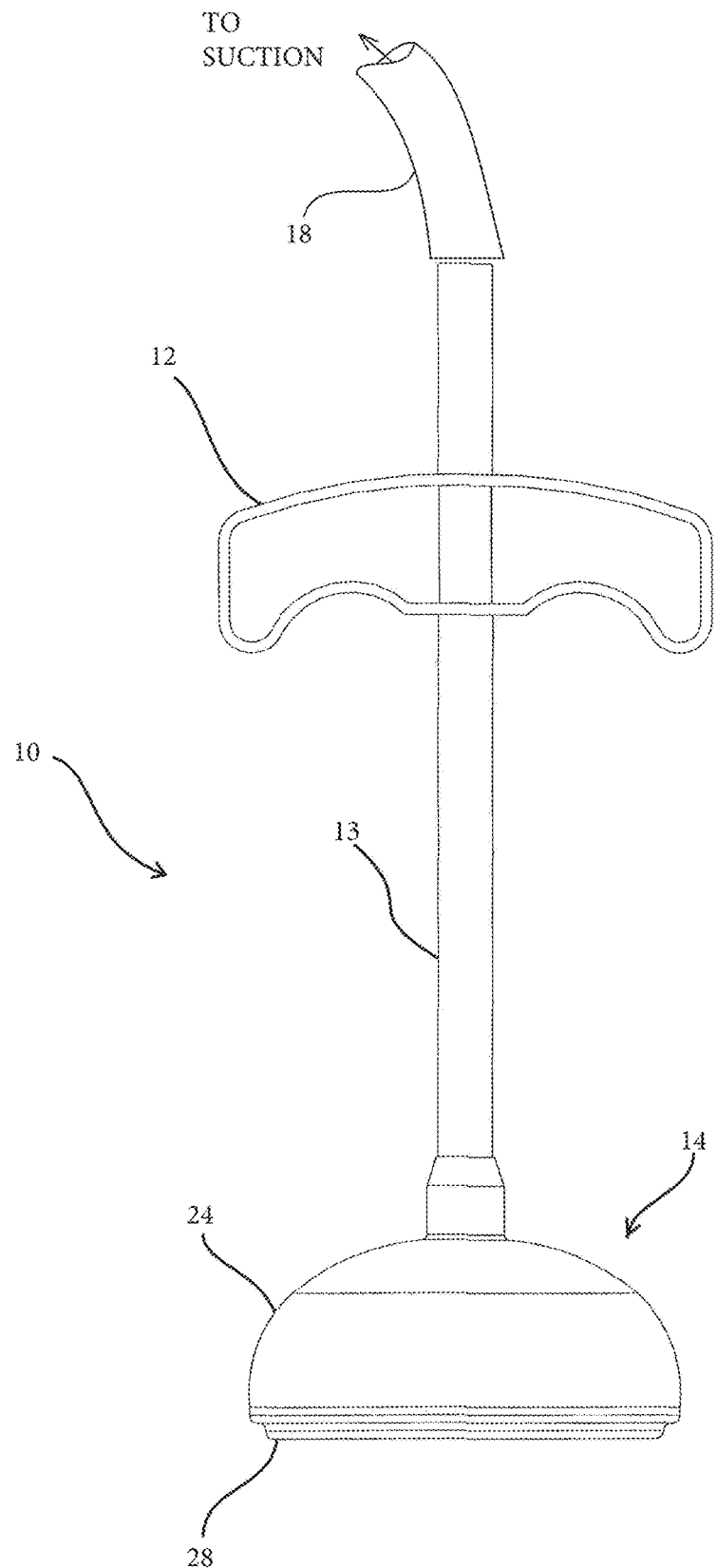
FIG. 12 is a perspective view of an embodiment of a surgical device having a channel disposed in a stem of the surgical device, a handle, and a suction head.
Figure 13:
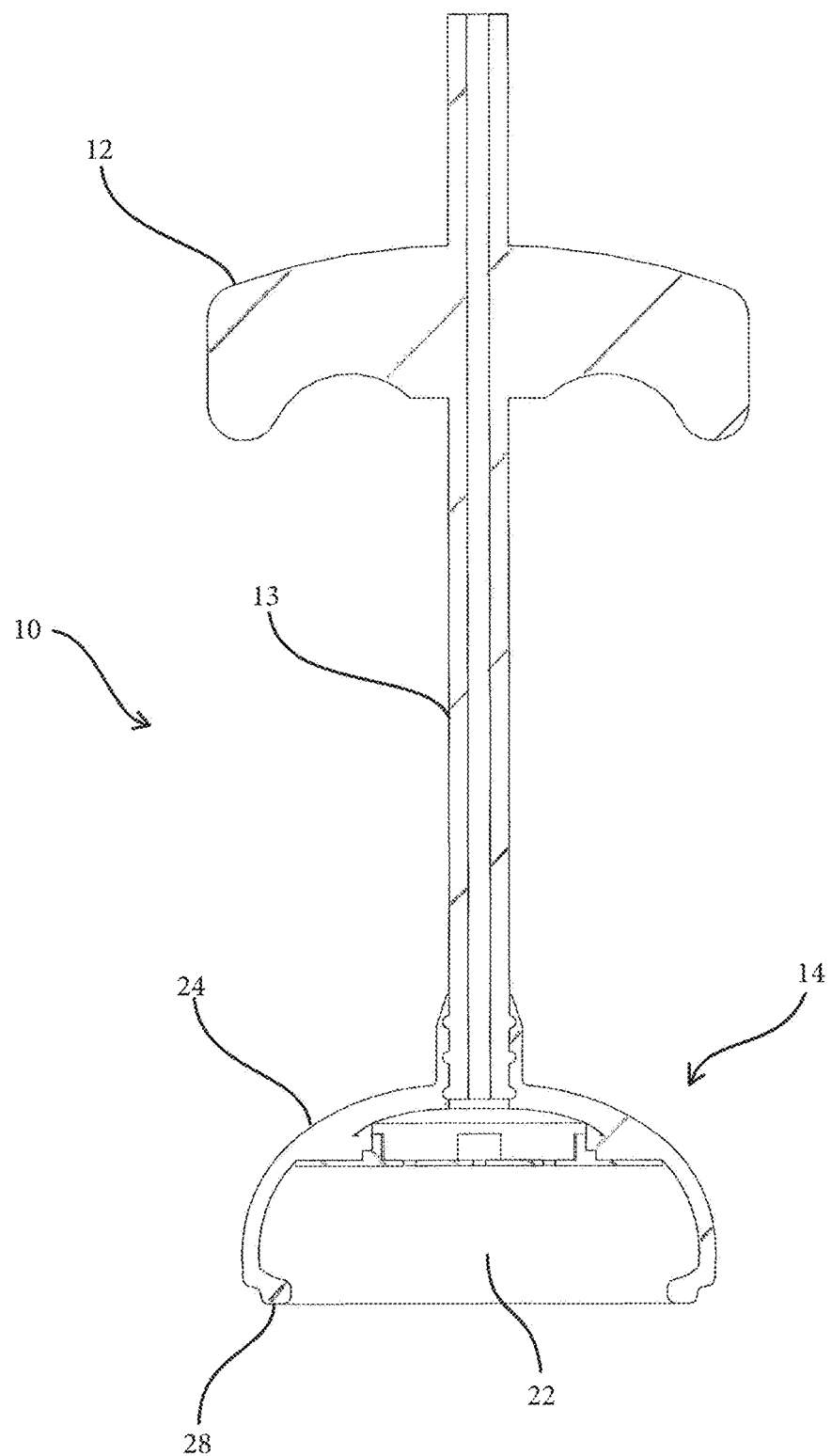
FIG. 13 is a sectional view of an embodiment of a surgical device having a channel disposed in a stem of the surgical device, a handle, and a suction head.

FIGS. 12 and 13 depict one embodiment which provides a low profile in which suction tubing 18 may be coupled to a distal end of the stem 13, opposite the suction head 14.

Figure 14:
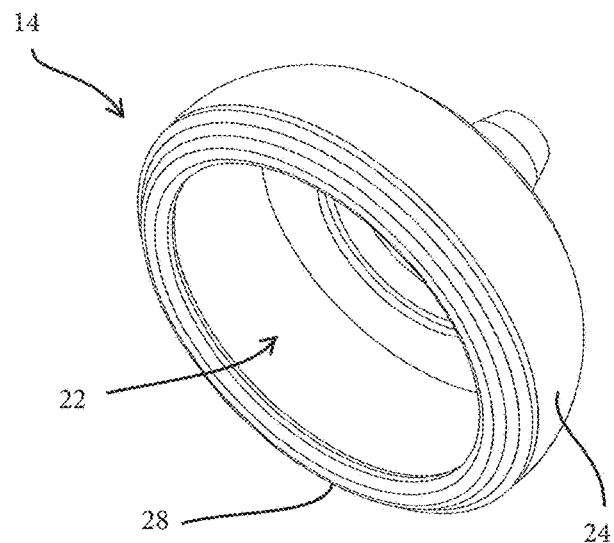
FIG. 14 is a perspective view of an embodiment of a suction head.
Figure 15:
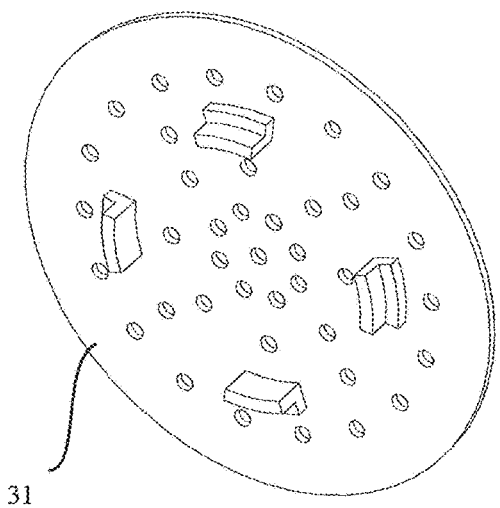
FIG. 15 is a perspective view of an embodiment of a disc.
Figure 16:
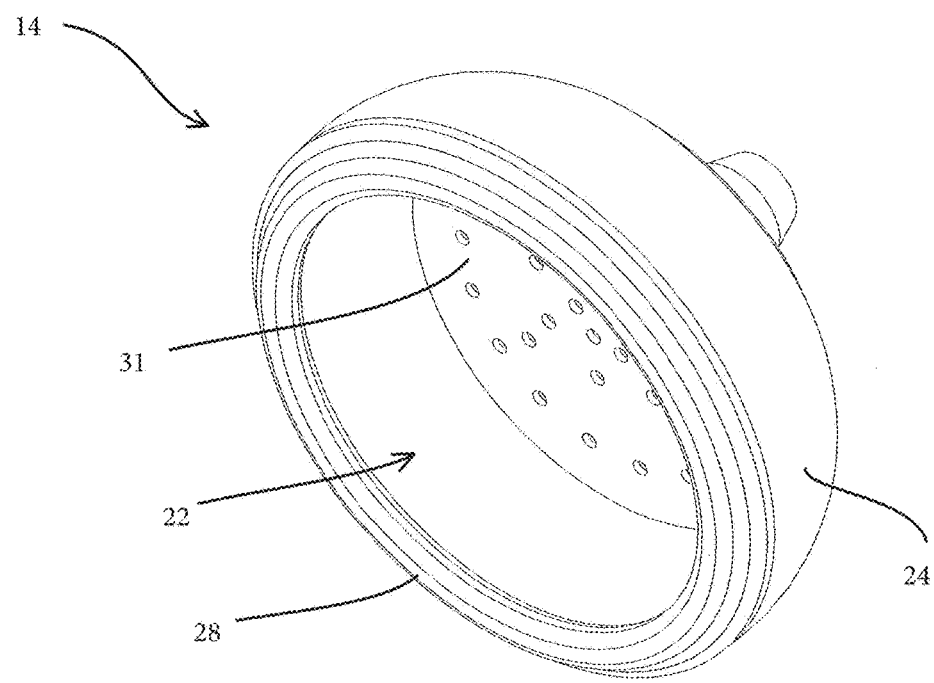
FIG. 16 is a perspective view of an embodiment of a disc disposed inside a suction head.

FIGS. 14-16 depict suction heads 14 and a disc 31 which is deployable in the suction head 14. The disc 31 may be inserted in the suction head 14 to provide a rigid support to the suction head 14 to prevent collapse of the suction head 14 when the suction chamber 22 is in fluid communication with the negative pressure source and when there is negative pressure in the suction head 14 relative to atmospheric pressure. As can be seen in FIGS. 14 and 16, the contact surface 28 of the suction head 14 may have profiles optimized for contacting and maintaining a negative pressure seal between the device 10 and a patient. Various profiles and surface textures may be used to achieve appropriate contact between the device 10 and a patient's tissue and will be understood by one of skill in the art to modify the contact surface 28 for various purposes.

Some embodiments include a pressure gauge (not shown) in fluid communication with the suction chamber 22. The pressure gauge is operable to detect pressure levels in the device 10 and display the pressure levels to a user. The pressure gauge may be positioned on the suction head 14, on the stem 13, or on the handle 12. A portion of the pressure gauge must be in fluid communication with the suction chamber 22 to display the pressure levels that are present in the suction chamber 12. Specifically, the pressure gauge allows a user to determine if the negative pressure in the suction chamber 22 is sufficient (or excessive) to manipulate a patient's tissue when the contact surface 28 is in contact with the patient's tissue and air has been removed from the suction chamber 22 resulting in negative pressure in the suction chamber 22.

Figure 17:
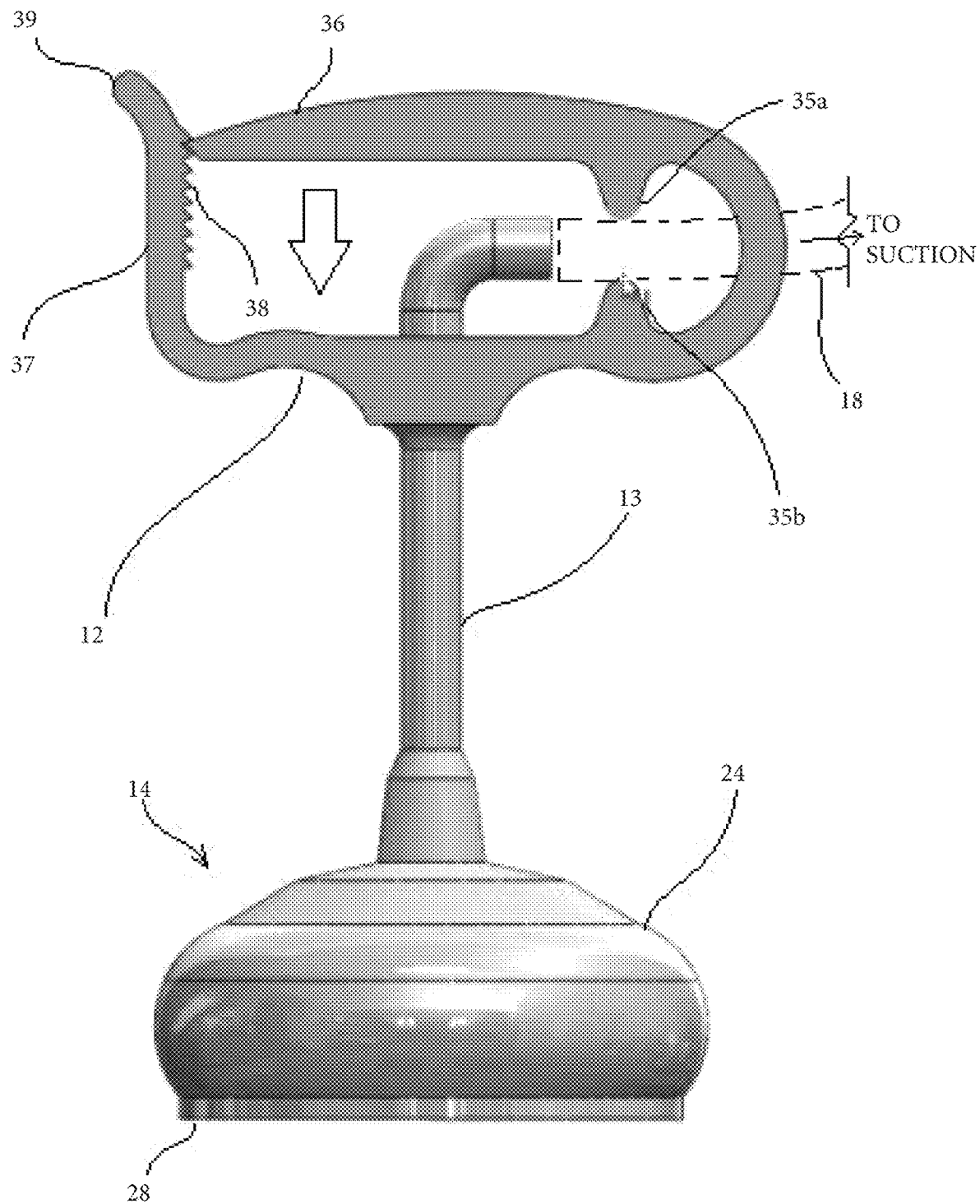
FIG. 17 is a perspective view of an embodiment of a surgical device having a channel disposed in a stem of the surgical device, a handle also acting as a hose clamp, and a suction head.

In other embodiments, the handle 12 may act as a mechanism for cutting off fluid communication between the source of negative pressure and the suction chamber 22, as shown in FIG. 17. For example, the device comprises a suction head 14 coupled to a stem 13. A channel (not shown) disposed in the stem 13 and the suction head 14 are in fluid communication. A handle 12 is coupled to the stem 13. The stem 13 may be disposed about a channel. The handle 12 is also capable of acting as a hose clamp as shown. The stem 13 may be oriented along a vertical axis. At a distal end of the stem 13, the stem 13 may be oriented substantially perpendicularly to the vertical axis. The distal end of the stem 13 may be configured to couple to suction tubing 18. The handle 12 may be affixed to the stem 13. In this embodiment, a portion of the handle comprises a clamp lever 36. Another portion of the handle 12 comprises a clamp retainer 37. The clamp retainer 37 comprises clamp retainer teeth 38, such that when the clamp retainer 37 is naturally biased toward the clamp lever 36, the clamp retainer teeth 38 engage the clamp lever 36, thus preventing the clamp lever 36 from biasing. The handle 12 also comprises a retainer release 39 which may be optionally biased away from the clamp lever 36, thus disengaging the clamp retainer teeth 38 from the clamp lever 36. The handle also comprises at least one clamping surface 35 which is selectably moveable by manually biasing the clamp lever 36 because the clamping surface 35 is positioned on the clamp lever 36. In one embodiment, when the suction tubing 18 is coupled to the stem 13, the suction tubing 18 is positioned between two clamping surfaces 35. A first clamping surface 35a may be advanced toward a second clamping surface 35b by biasing the clamp lever 36 downward, thus advancing the first clamping surface 35a toward the suction tubing 18. The clamping surfaces 35 are operable to close or seal off fluid communication of the suction tubing 18, thus preventing fluid communication between the suction head 14 and a negative pressure source. The clamp retainer teeth 38 retain the clamp lever 36 in the desired position until a user manually biases the retainer release 39 to disengages the clamp retainer teeth 38 from the clamp lever 36. One of skill in the art may recognize other hose clamps that may be readily available for implementation with the device 10.

In other embodiments, the device 10 comprises suction tubing 18 coupled to a suction head 14 such that the suction tubing 18 and the suction head 14 are in fluid communication. The suction tubing 18 acts as the stem 13. A handle 12 may be disposed about the suction tubing 18 and the suction tubing 18 is reinforced to prevent collapse of the suction tubing 18 when negative pressure is introduced into the system.

Figure 18:
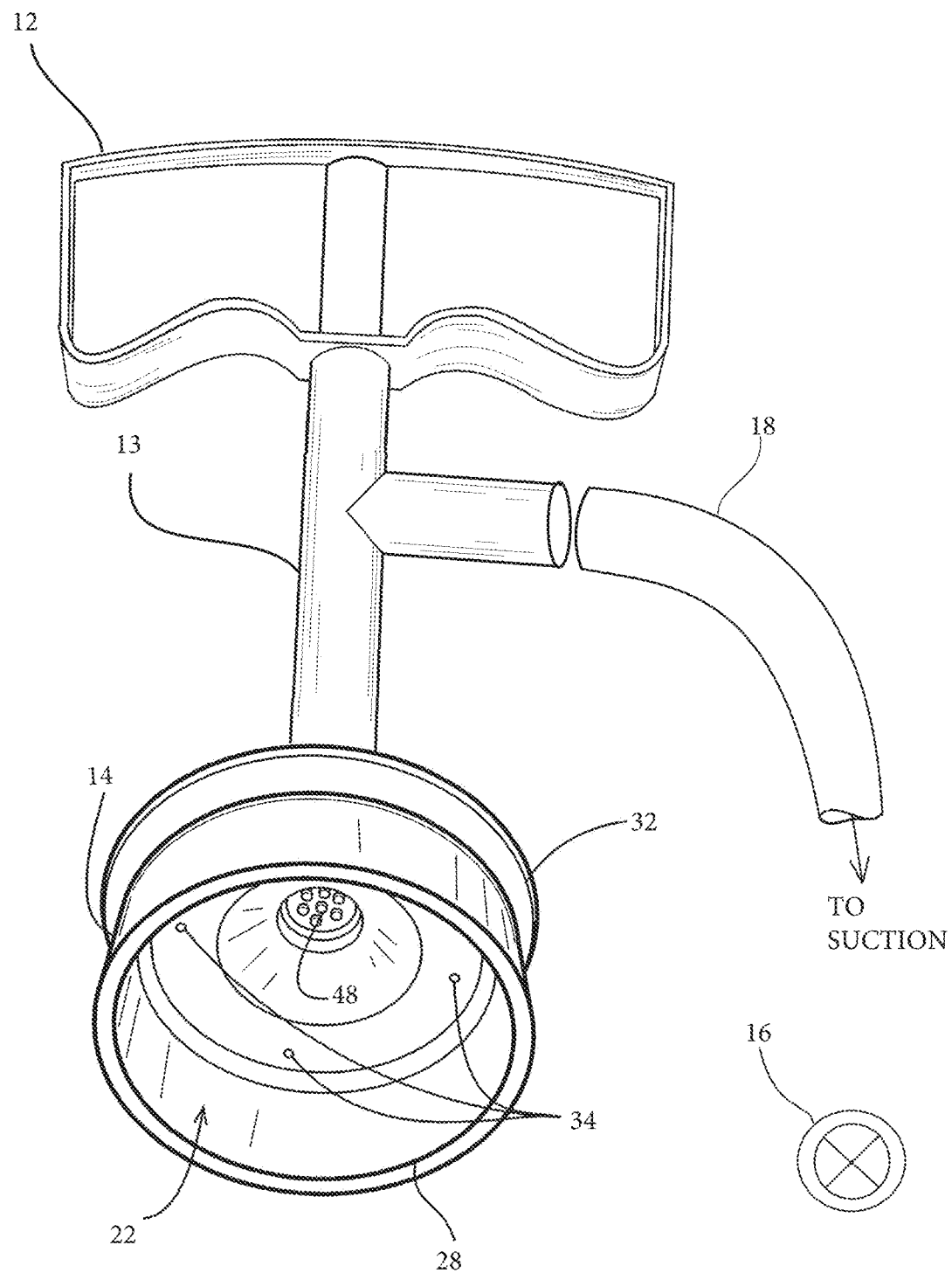
FIG. 18 is a perspective view of an embodiment of a surgical device having a channel disposed in a stem of the surgical device, a handle, and a suction head, the suction head having pressure release ports.

A number of various other embodiments may provide for the release of the negative pressure seal between the patient's body and the suction head 14. One or more pressure release ports 34, as shown in FIG. 18, are defined in suction head 14 in some embodiments. Each pressure release port 34 passes through the suction head 14 to allow gas transfer across suction head 14. When a negative pressure is pulled in suction chamber 22, pressure release 32 is held down against the exterior of suction head 14, thereby blocking entry of gas into the suction chamber. In such embodiments, the pressure release 32 is closed. An upturned edge around the perimeter of pressure release 32 provides a location for a user to manually lift the pressure release 32. When pressure release 32 is lifted away from suction head 14, one or more pressure release ports 34 are opened and the suction force created in suction chamber 22 is released as air enters suction chamber 22 quickly through the pressure release ports 34. The pressure release 32 provides a convenient way for a user to quickly release the suction of the device 10 against a patient during an operation. This embodiment may be especially relevant when the valve 16 is located on the suction tubing 18 or on the wall of a surgical suite, however, this embodiment may be used with a variety of embodiments and in a variety of configurations.

Figure 19:
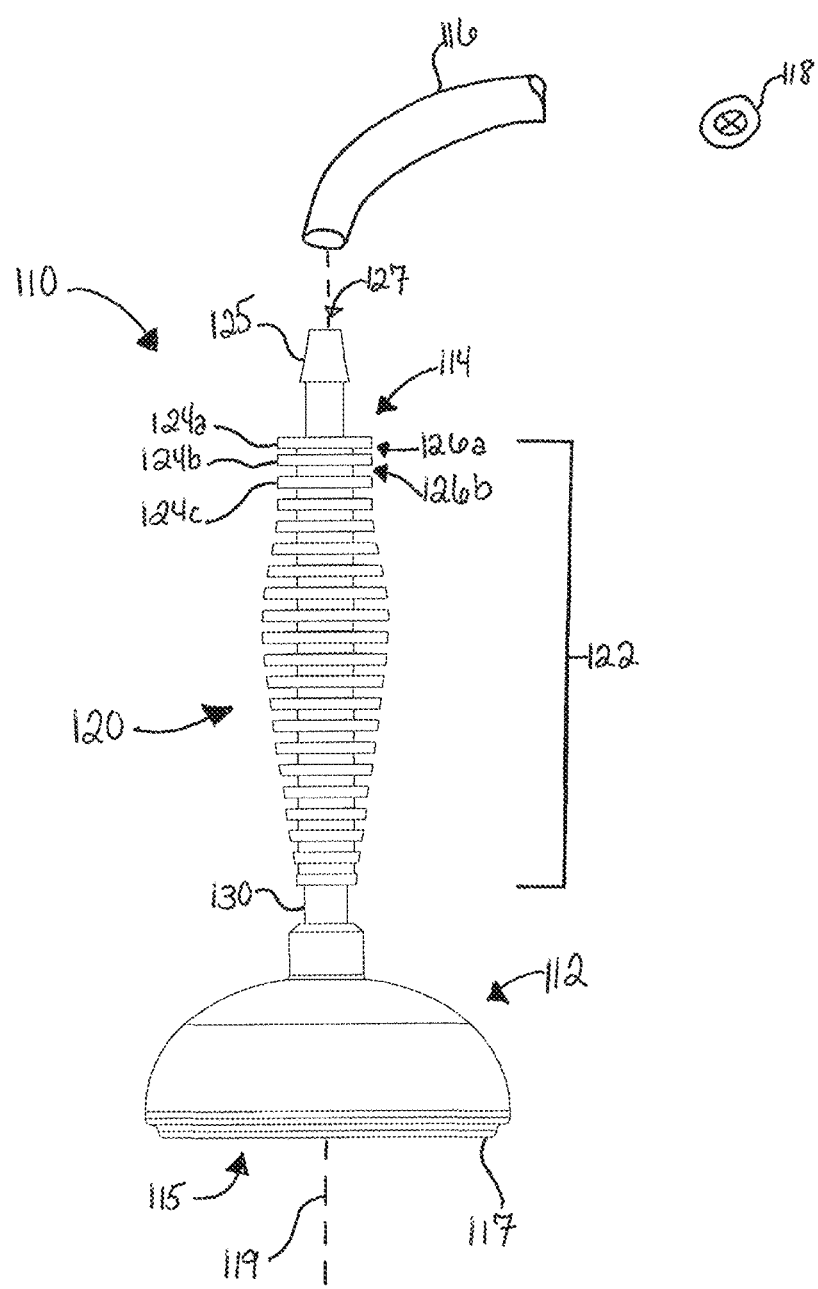
FIG. 19 is a side view of an embodiment of a surgical device having a stem, a handle, a suction head, and an articulating joint.

Referring to FIG. 19, an embodiment of a surgical device is shown in a side view. Device 110 includes a suction head 112 and a stem 114 extending from the suction head 112. Suction tubing 116 may be coupled to a source having negative pressure, thus providing suction to the suction tubing 116. A valve 118 may be disposed on the suction tubing 116, at the negative pressure source, or on a wall of the surgical suite. The valve 118 is operable to permit fluid communication between the suction head 112 and negative pressure source via the suction tubing 116 and stem 114 when suction tubing 116 is coupled to stem 114 of the device 110. When the suction tubing 116 is coupled to the stem 114 of the device 110 and the valve 118 is configured in an open position, air may be pulled from the interior of the suction head 112 (a suction chamber 115) and through the suction tubing 116.

In some embodiments, as shown in FIG. 19, the device 110 may include a handle 120 disposed about the stem 114. During use, a user may grasp handle 120 while suction head 112 engages a patient's body. Suction head 112 can define an open suction chamber 115. The suction head 112 may further comprise a contact surface 117. The contact surface 117 of the suction head 112 may be positioned to engage a patient's body via negative pressure in the suction chamber 115. When the contact surface 117 of the suction head 112 is positioned against a patient's body and the source having negative pressure is in fluid communication with the suction chamber 115 via the suction tubing 116, a negative pressure can be drawn between the suction head 112 and the patient's body. The contact surface 117 may operate as a seal between the patient's tissue and the suction head 112. Once a negative pressure suction force is established between the device 110 and the patient via the suction head 112, the user may then use the handle 120 to manually lift the patient's tissue while maintaining a negative pressure seal between the patient's body and the suction head 112. When the proper negative suction force has been achieved, a user may close the valve 118 such that negative pressure source and the suction head 112 are no longer in fluid communication. Once tissue is lifted, the user may then insert a trocar or Veress needle using any suitable insertion technique.

Figure 20:
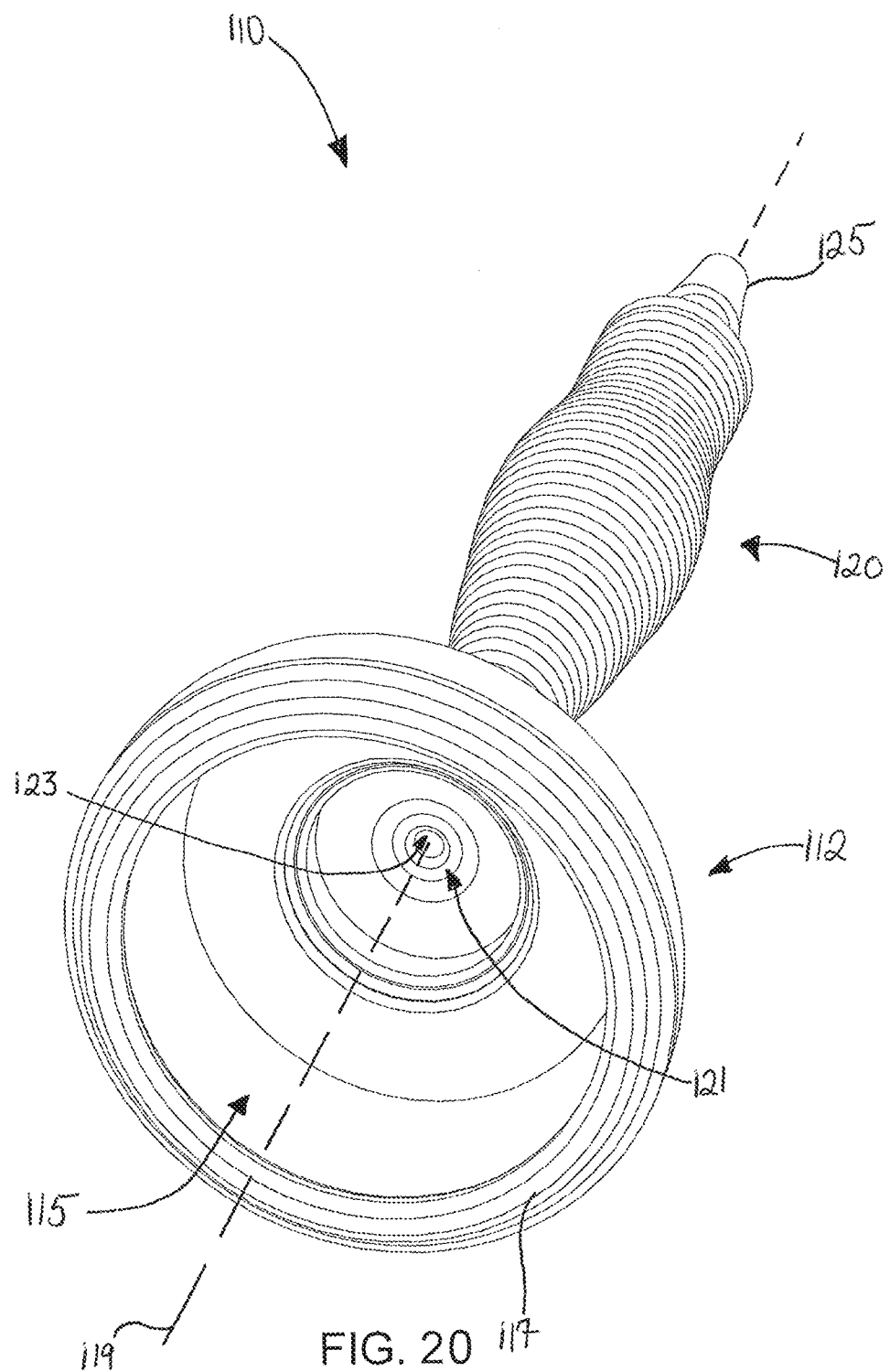
FIG. 20 is a perspective view of an embodiment of a surgical device with a suction head defining a suction chamber.
Figure 21:
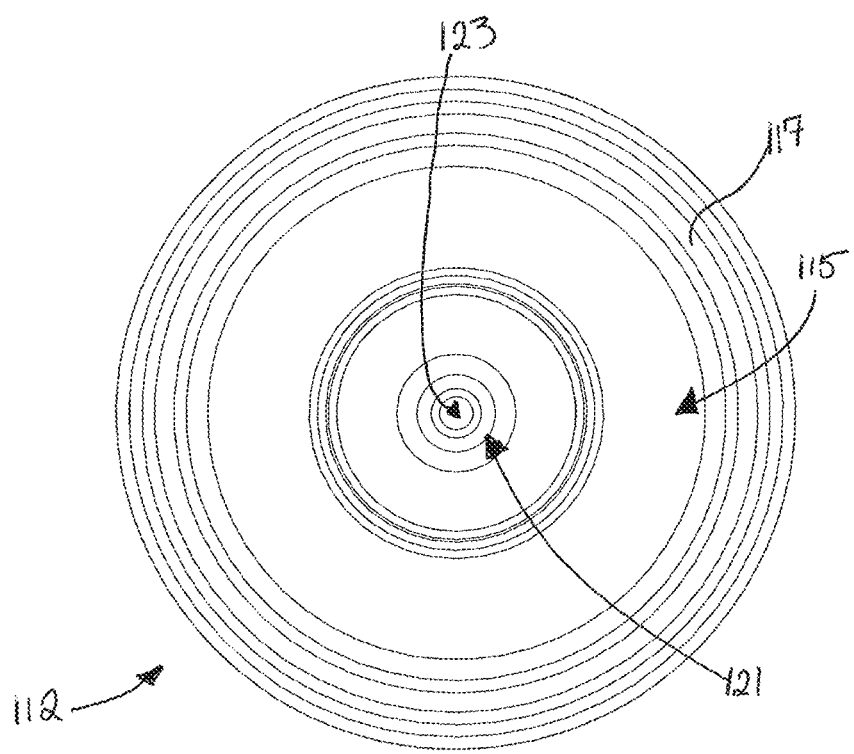
FIG. 21 is a bottom view of an embodiment of suction head defining a suction chamber in fluid communication with a channel.

Referring to FIG. 20, in an embodiment, a suction head 112 is provided on the device 110. The suction head 112 includes a suction chamber 115 disposed within or on the suction head 112 and a contact surface 117. The contact surface 117 may be disposed on the suction head 112 on the open end of the suction chamber 115. The contact surface 117 may include a non-uniform surface as can be seen in FIG. 19-21. Specifically, the non-uniform surface may include concentric circles radiating out from a longitudinal axis 119. The contact surface 117 may include the concentric circles defining the profile of the contact surface 117, wherein the concentric circles are centered on the longitudinal axis 119 and may be disposed at different positions along a length of the longitudinal axis 119.

One embodiment of the interior of the suction head 112 defining the suction chamber 115 is depicted in FIGS. 20 and 21. In some embodiments, the suction chamber 115 is disposed within the suction head 112 such that the suction chamber 115 spans portions of the suction head 115 with varying diameters at varying depths. With reference to FIG. 20, the suction chamber 115 may have the largest diameter near the contact surface 117 of the suction head 112 relative to portions of the suction chamber 115 distal the contact surface 117.

As can further be seen in FIGS. 20 and 21, a suction head port 121 can be disposed in the suction head 112. The port 121 may provide a passageway through which air may be communicated to and away from the suction head 112 via a channel 123 disposed in the stem 114. The port 121 may be disposed through the wall of the suction head 112. The port 121 can be positioned in the suction head 112 at an end of the suction head 112 distal from the contact surface 117.

Figure 22:
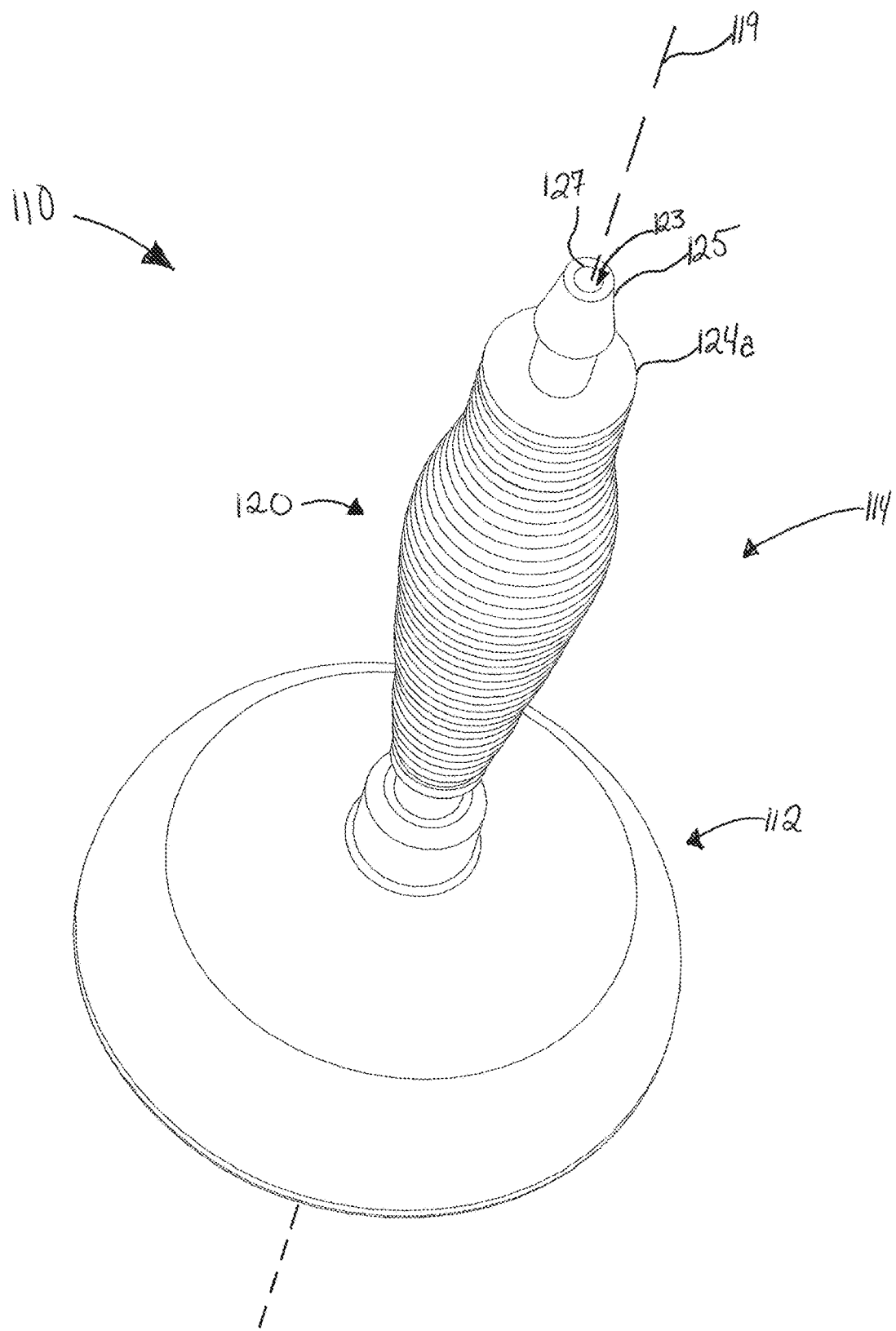
FIG. 22 is a perspective view of an embodiment of a surgical device having a fitting extending from the stem.
Figure 23:
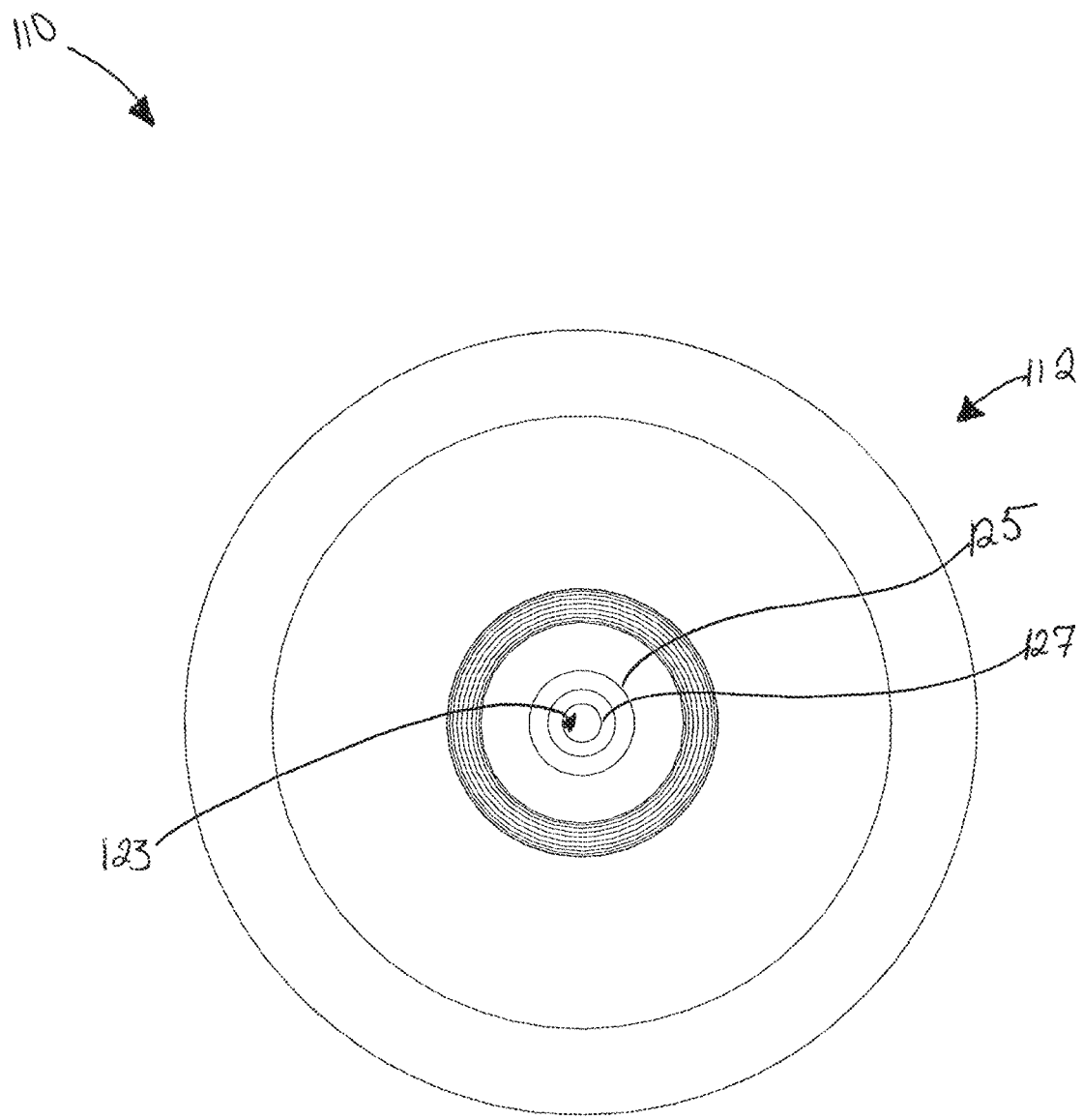
FIG. 23 is a top view of an embodiment of a surgical device stem extending from a suction head, the stem having a channel disposed therein.

Now referring to FIGS. 22 and 23, in one embodiment, a stem 114 is provided such that the stem 114 extends from the suction head 112. The stem may include a fitting 125. The fitting 125 may be configured to couple to suction tubing 116. The fitting 125 includes an open end 127. The open end 127 may be in fluid communication with a channel 123. Thus the open end 127 can be in fluid communication with the suction chamber 115 via the channel 123. The fitting 125 may comprise a variety of mechanical systems for fastening suction tubing 116 to a surgical device 110. For example, FIG. 22 demonstrates a barbed connector. Other fittings may be implemented in each embodiment including bayonet connectors, compression fittings, threaded connectors, bores, luer locks, pipe thread connectors, panel mounts, quick disconnect couplings, and any other coupling as one of ordinary skill in the art would recognize.

Figure 24:
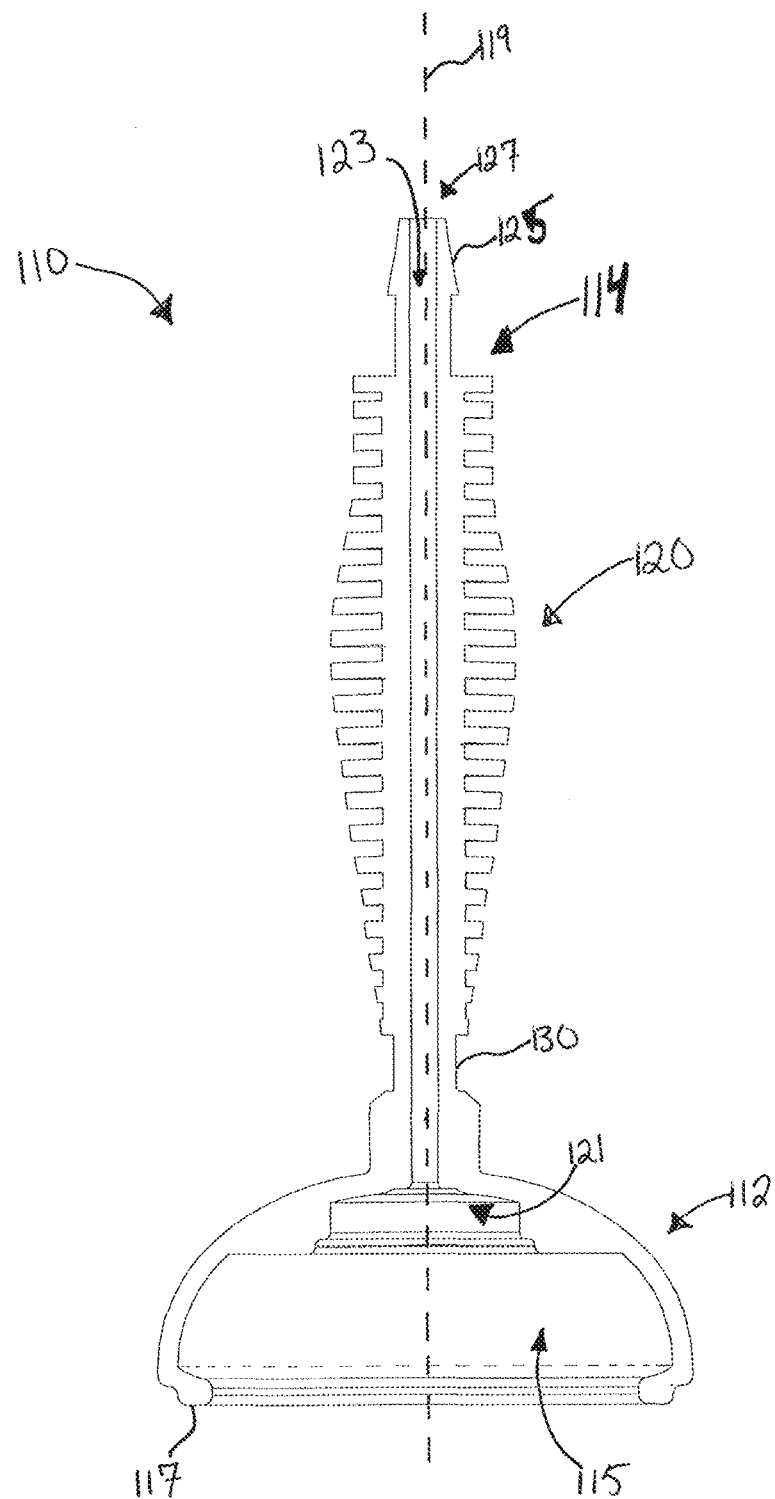
FIG. 24 is a cross-section side view of an embodiment of a surgical device.

Now referring to FIG. 24, a sectional side view of the device 110 is provided. As previously discussed, the device 110 includes a stem 114 extending from a suction head 112. The stem 114 and suction head 112 are disposed about a longitudinal axis 119. A channel 123 is disposed within the stem 114 about the longitudinal axis 119. The channel 123 is in fluid communication with the suction chamber 115 via the port 121 of the suction head 112. The channel 123 may also be in fluid communication with a negative pressure source via a vacuum hose 116 and the open end 127 of the fitting 125. An articulating joint 130 may be disposed between the contact surface 117 of the suction head 112 and the distal end of the stem 114.

Figure 25:
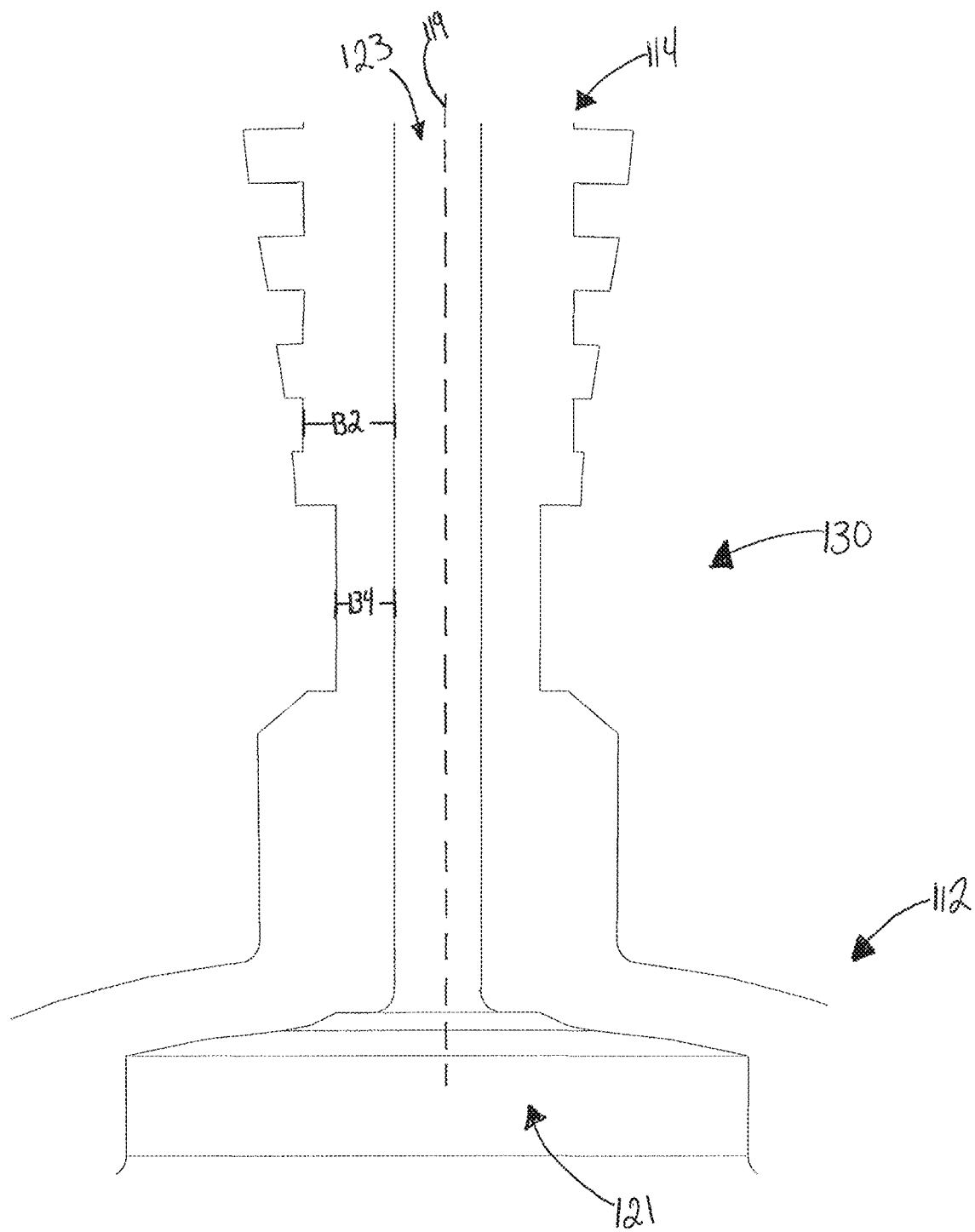
FIG. 25 is an expanded cross-section side of an embodiment of a surgical device having an articulating living hinge.

Referring now to FIG. 25, in one embodiment, the articulating joint 130 can be formed on the device 110 between the suction head 112 and the stem 114. In some embodiments the articulating joint 130 is formed directly on the stem 114. In some embodiments, the articulating joint 130 is a living hinge, meaning made from the same material as the two elements adjacent the living hinge, thus the hinge is formed together with the connecting elements. The articulating joint 130 can permit the suction head 112 and the stem 114 to articulate, move, or pivot with respect to each other. When the device 110 is in a resting or neutral position, the longitudinal axis 119 runs through the center of the device 110, such that the channel 123, the stem 114, and the suction head 112 are all disposed or centered about the longitudinal axis 119. When a force is applied to the device 110 that is not parallel to the longitudinal axis 119 and only on one side of the device 110 relative to the articulating joint 130, the articulating joint 130 may be able to move or deform such that the stem 114 and the suction head 112 are able to articulate relative to each other.

With further reference to FIG. 25, in some embodiments, the articulating joint 130 can include the channel 123 extending through the articulating joint 130. As can be seen in FIG. 25, the side walls may have varying thickness throughout the body of the device 1110. Specifically, the stem 114 has a baseline stem wall thickness 132. The articulating joint 130 may have a second articulating joint wall thickness 134. The thickness of the walls is measured between the inside surface of the device 110 defined in the channel 123 and extends to the outside surface of the respective element. The articulating joint wall thickness 134 is less than the stem wall thickness 132. This provides the ability for the articulating joint 130 to flex and bend. However, in this embodiment the articulating joint wall thickness 134 is sufficiently thick to prevent the channel 123 from collapsing due to negative pressure, bending, etc. For example, the articulating joint wall thickness 34 might be between 0.05 and 0.12 inches thick of vinyl material. In other embodiments, the articulating joint wall thickness 134 might be between 0.07 and 0.09 inches thick of vinyl material. Other materials may be used in accordance with this disclosure and the thickness of the walls may be varied according to the properties of the material in order to achieve the appropriate articulation. The stem wall thickness 132 might be between 0.2 and 0.3 inches thick of vinyl material. In other embodiments, the stem wall thickness 132 might be between 0.23 and 0.26 inches thick of vinyl material.

In some embodiments, the device 110 may be a single molded piece. For example, plastic injection molding and 3-D printing techniques may be implemented to form a single-piece, integral device 110. However, it is within the scope of this disclosure that the articulating joint 130 can also be a mechanical joint to which the other elements of the device 110 are coupled.

Figure 26:
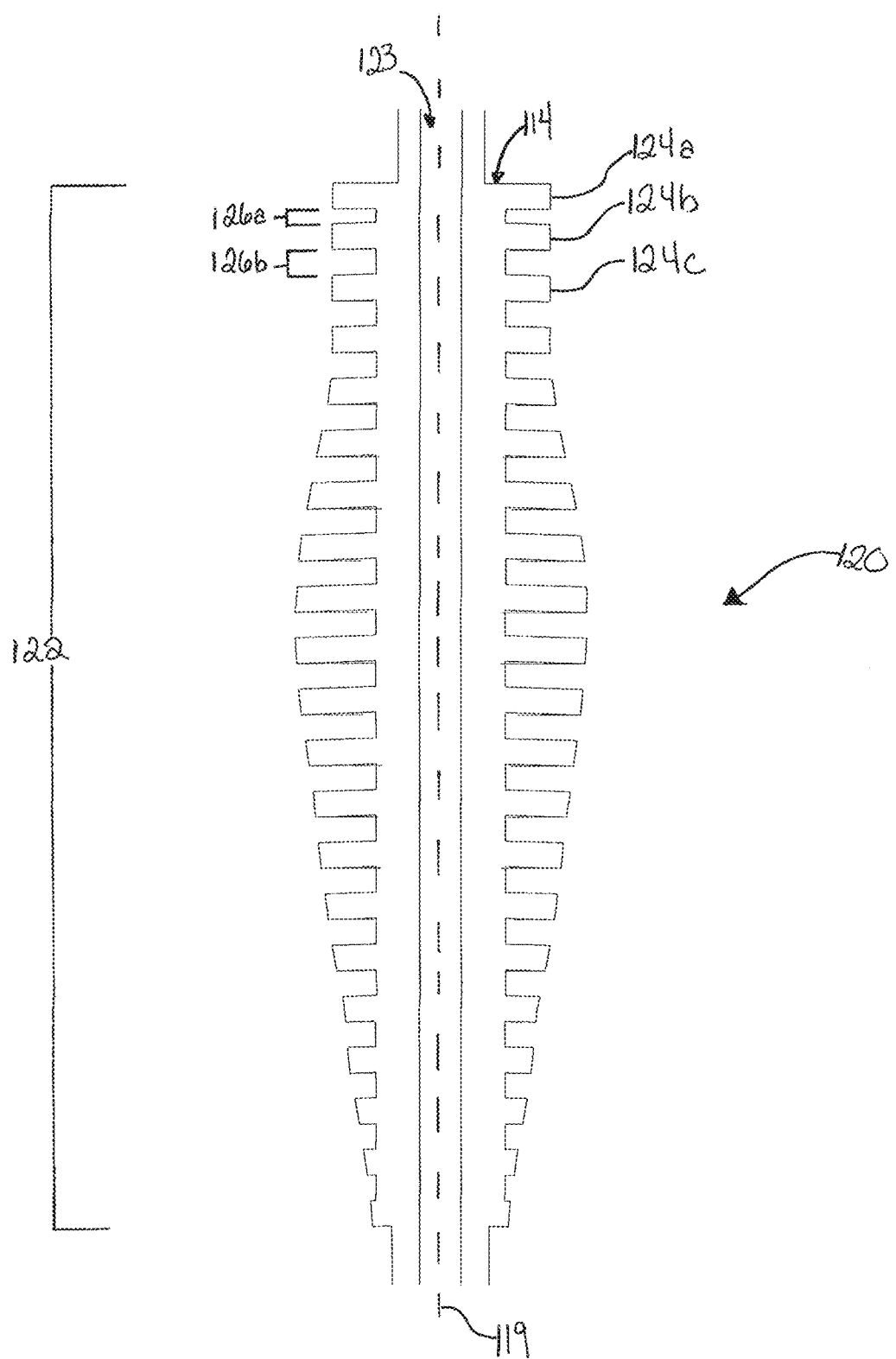
FIG. 26 is an expanded cross-section side view of an embodiment of a surgical device having a handle comprising a plurality of ribs.

Now referring to FIG. 26, a handle 120 is provided. The handle 120 may be disposed about the longitudinal axis 119. In some embodiments, the handle 120 may be formed directly around the channel 123. In other embodiments, the handle 120 can be formed around or coupled to the stem 114. The handle 120 may be formed in a variety of methods and shapes. As can be seen in both FIGS. 19 and 26, the handle 120 may include a plurality of ribs 122 extending from the stem 114. The plurality of ribs 122 may each be of uniform thickness. The plurality of ribs 122 may also be evenly spaced longitudinally along the longitudinal axis 119 or stem 114. In other embodiments, the spacing between the first rib 124a and the second rib 124b may be less than the spacing between the remaining ribs of the plurality of ribs 122. The terms ridges or flanges may be used interchangeably with ribs.

For example, the plurality of ribs 122 may include a first rib 124a, a second rib 124b, and a third rib 124c, and wherein a first space 126a is defined between the first rib 124a and the second rib 124b having a first length and a second space 126b is defined between the second rib 124b and the third rib 124c having a second length, the first length of the first space 126a being less than the second length of the second space 126b. In some embodiments, the first space 126a defined between the first rib 124a and the second rib 124b is between 0.02 to 0.06 inches and the second space 126b between the second rib 124b and the third rib 124c and all subsequent spaces between the remaining ribs of the plurality of ribs 122 is between 0.05 and 0.1 inches. In other embodiments the first space 126a defined between the first rib 124a and the second rib 124b is between 0.035 to 0.045 inches and the second space 126b between the second rib 124b and the third rib 124c and all subsequent spaces between the remaining ribs of the plurality of ribs 122 is between 0.07 and 0.08 inches.

Referring further to FIG. 26, the handle 120 may be shaped such that the handle 120 can conform to the profile or shape of a user's hand. Each of the plurality of ribs 122 may extend from the device 110 a different length such that a general grip profile is formed for the handle 120. The plurality of spaced ribs 122 may define a contour which is configured to match the contour of a user's hand. The spaces between each of the plurality of ribs 122 may provide or may be capable of providing greater traction. For example, a user may be performing a surgery in which fluids are present. The plurality of ribs 122 can provide enhanced traction for the user when gripping the handle 120.

Furthermore, the handle 120 may be disposed about the longitudinal axis 119. Having the handle 120 disposed about the longitudinal axis 119 can provide a user with a more ergonomic grip on the handle 120. For example, when a user is operating on a patient, the patient is generally resting at a height close to the user's waist. The user may be manipulating tissue in a variety of directions. However, if the contact point with the patient is substantially anterior the user, a handle 120 positioned on the device 110 about the longitudinal axis 119 can allow the user to maintain an ergonomic and comfortable grip on the handle 120 and device 110 which does not strain or require the user to maneuver his/her own arms and hands into anatomically difficult and uncomfortable positions.

Referring generally to the device 110, the various components may be integrated into a single piece, as shown in FIG. 20, whereas other embodiments may have each piece being formed separately and subsequently assembled. When the device 110 is one integral piece, the device may be formed or molded out of a single material. In other embodiments, the device 110 may be formed of separate parts and materials, for example the device 110 may be overmolded with a second material such as silicone. Any combination of formed or integrated parts may be implemented as known by one of skill in the art.

In some embodiments, the stem 114 can be rigid. Thus, when the suction head 112 is in a negative pressure seal with the patient's tissue and a user is manipulating a patient's tissue in a procedure or operation, the suction head 112 can follow the movement of the handle substantially proportionally, thus allowing the user a high level of control over the device 110 and the patient's tissue under the negative pressure seal with the device 110.

In embodiments when the manipulation of a patient's tissue may require more than translation along the direction of the applied force alone, the stem 114 may comprise a semi-flexible material, thus allowing the user to apply a torqueing force to the device 110 that is at least partially translated to the patient's tissue. In this application, the user may use a torqueing force to properly position the user's hands to prevent interference with any procedures such as trocar insertion or Veress needle insertion during a laparoscopic surgical procedure using the device 110.

The stem 114 and the other components of the device 110 may be formed from a variety of materials most suitable for the desired rigidity or flexibility in the stem 114. Those of ordinary skill in the art will recognize numerous materials that may be used in the construction of the stem including ABS, Acrylic, HDPE, Polyester, Nylon, PET, LDPE, PS, PP, PVC, PTFE, etc.

Figure 27:
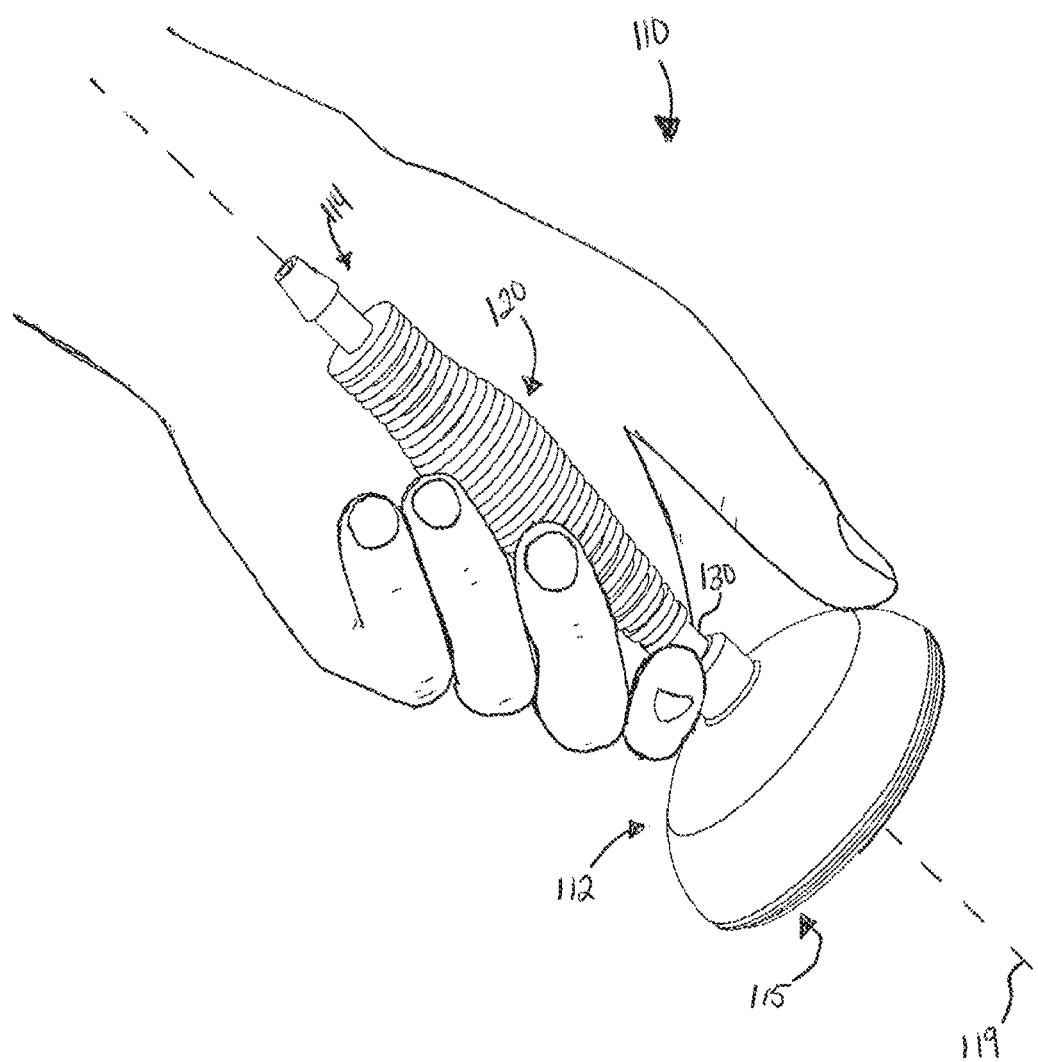
FIG. 27 is side view of a user implementing a first gripping position for grasping an exemplary embodiment of a surgical device having a handle disposed about a longitudinal axis.

Referring now to FIG. 27, a user may grasp the stem 114 of the device 1110, such that the user's hand surrounds the stem 114 and is oriented about the longitudinal axis 119. In this embodiment, the handle 120 is also disposed about the stem 114 and the longitudinal axis 119 and provides a surface for a user and the hand of a user to contact and grasp the device 110. FIG. 27 demonstrates a first gripping position such that the thumb of a user's hand is oriented along the handle 120 with the tip of the thumb oriented toward the suction head 112. The first gripping position can allow a user's hand and wrist to be oriented in a more mechanically neutral position than other embodiments in which the handle 120 is oriented perpendicular to the longitudinal axis 119. Furthermore, when performing a pulling motion with the device 110 to manipulate a patient's tissue in the first gripping position, the user's muscles which are engaged to perform the pulling motion are engaged more effectively, including the user's triceps brachii muscle.

Figure 28:
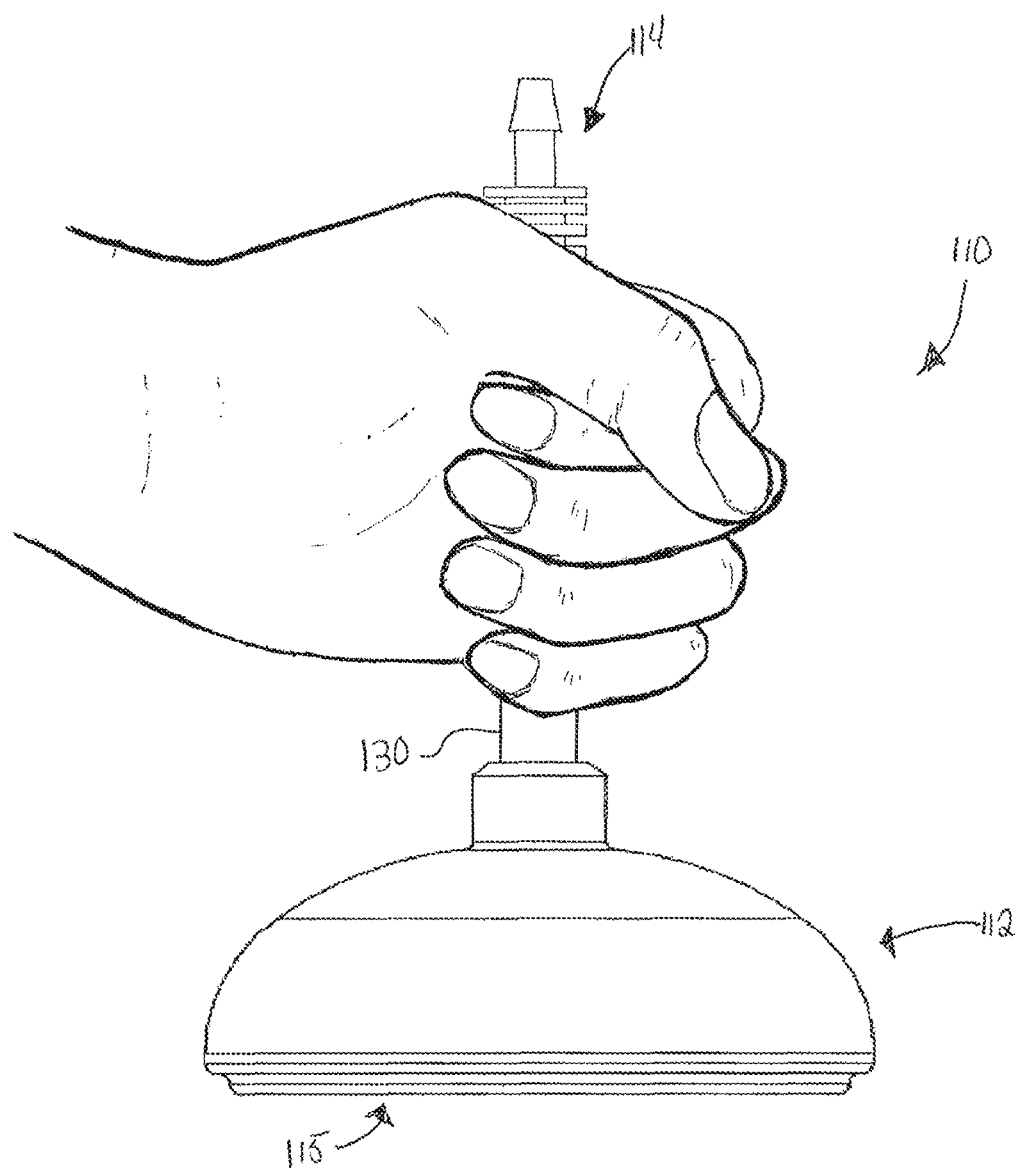
FIG. 28 is a side view of a user implementing a second gripping position for grasping an exemplary embodiment of a surgical device having a handle disposed about a longitudinal axis

Referring to FIG. 28, a second gripping position is demonstrated. In the second gripping position, the user's hand surrounds the stem 114 and is oriented about the longitudinal axis 119. In this embodiment, the handle 120 is also disposed about the stem 114 and the longitudinal axis 119 and provides a surface for a user and the hand of a user to contact and grasp the device 110. The second gripping position positions the user's hand such that the ulnar portion of a user's hand is oriented toward the suction head 112. The second position can allow the user to manipulate the patient's tissue from various angles while maintaining the user's hand and wrist in an anatomically neutral or comfortable position. Furthermore, the range of motion and effectiveness of engaging the user's muscles in order to manipulate the patient's tissue is increased for certain configurations, as demonstrated at least by FIG. 28.

Thus, although there have been described particular embodiments of the present invention of a new and useful LAPAROSCOPIC SURGICAL INSTRUMENT, it is not intended that such references be construed as limitations upon the scope of this invention.

What is claimed is:

1. A surgical device, comprising:
a stem defining a channel, the stem having a distal end and a proximate end;
a suction head extending from the proximate end of the stem and defining a suction chamber in fluid communication with the channel, the suction head having a non-uniform contact surface with a plurality of concentric circles formed at different longitudinal positions on the suction head;
a suction head port defined inside the suction head between the channel and the suction chamber, the suction head port positioned to provide a passageway through which fluid may be communicated between the channel and the suction head;
an articulating joint disposed between the suction head and the proximate end of the stem;
a longitudinal axis about which the channel and the stem are disposed;
a handle on the stem disposed around the stem and disposed about the longitudinal axis, the handle comprising a plurality of longitudinally spaced ribs extending from the stem, the handle extending from the distal end of the stem to the proximate end of the stem at the articulating joint,
wherein the longitudinally spaced ribs are spaced relative to each other along the longitudinal axis and are positioned around the stem,
wherein the longitudinally spaced ribs extend varying lengths from the stem to form a contoured grip profile shaped to match a contour of a user's hand, and
wherein the handle is positioned around the stem providing a first gripping position on the handle such that a thumb of the user's hand is oriented along the handle with a tip of the thumb toward the suction head and providing a second gripping position on the handle such that an ulnar portion of the user's hand is oriented toward the suction head.

2. The surgical device of claim 1, wherein the stem, the suction head, the handle comprising the longitudinally spaced ribs, and the articulating joint are injection molded and are an integral unit.

3. The surgical device of claim 2, wherein the articulating joint includes joint side walls of a first thickness and the stem includes stem side walls of a second thickness, wherein the second thickness of the stem side walls is greater than the first thickness of the joint side walls.

4. The surgical device of claim 1, wherein the articulating joint is a living hinge configured to articulate such that the stem pivots relative to the suction head.

5. The surgical device of claim 4, wherein the living hinge is an annular living hinge.

6. The surgical device of claim 1, wherein the distal end of the stem includes a fitting.

7. The surgical device of claim 1, wherein the surgical device is formed from a polymer.

8. The surgical device of claim 1,
wherein the handle is disposed about the longitudinal axis such that when a user grips the handle in the second gripping position, the hand of the user is disposed about the longitudinal axis and the ulnar portion of the user's hand is oriented toward the suction head.

9. A surgical device, comprising:
a stem defining a channel and disposed about a longitudinal axis, the stem having a distal end and a proximate end, and the stem having a stem wall thickness;
a suction head extending from the proximate end of the stem and defining a suction chamber in fluid communication with the channel, the suction head having a non-uniform contact surface with a plurality of concentric circles formed at different longitudinal positions on the suction head; and
an articulating joint between the stem and the suction head, the articulating joint having an articulating joint wall thickness less than the stem wall thickness;
a handle on the stem extending from the distal end of the stem to the articulating joint and positioned around the stem along the longitudinal axis, the handle providing a first gripping position such that a thumb of a user's hand is oriented along the handle with a tip of the thumb toward the suction head and providing a second gripping position on the handle such that an ulnar portion of the user's hand is oriented toward the suction head,
wherein the handle comprises a plurality of longitudinally spaced, annular ribs extending from the stem around the stem and spaced relative to each other along the longitudinal axis,
wherein the plurality of longitudinally spaced, annular ribs extend varying lengths from the stem to form a contoured grip profile, and
wherein the plurality of longitudinally spaced, annular ribs includes at least a first rib, a second rib, and a third rib, and wherein a first space is defined between the first rib and the second rib having a first length along the longitudinal axis and a second space is defined between the second rib and the third rib having a second length along the longitudinal axis, the first length of the first space being less than the second length of the second space.

10. The surgical device of claim 9, wherein the stem, the suction head, the articulating joint, and the handle comprising the longitudinally spaced ribs are injection molded and are an integral unit.

11. The surgical device of claim 9, wherein the first rib is disposed between the second rib and the distal end of the stem.

12. The surgical device of claim 9, wherein the contoured grip profile is configured to match a user hand contour.

13. The surgical device of claim 9,
the handle is disposed about the longitudinal axis such that when the user grips the handle in the second gripping position, the hand of the user is disposed about the longitudinal axis and the ulnar portion of the user's hand is oriented toward the suction head.

14. The surgical device of claim 9, wherein the articulating joint includes joint side walls having the articulating joint wall thickness and the stem includes stem side walls having the stem wall thickness.

15. A surgical device for engaging patient tissue via negative pressure from a negative pressure source, comprising:
- a suction head defining a suction chamber, the suction head having a contact surface for engaging the patient tissue;
- an articulating joint extending from the suction head;
- a stem extending from the articulating joint and disposed about a longitudinal axis, the stem defining a channel configured to be in fluid communication with the negative pressure source;
- a vacuum fitting disposed on the stem; and
- a handle on the stem positioned around the stem along the longitudinal axis, the handle extending from the articulating joint to the vacuum fitting, the handle providing a first gripping position such that a thumb of a user's hand is oriented along the handle with a tip of the thumb projecting toward the suction head and providing a second gripping position on the handle such that an ulnar portion of the user's hand is oriented toward the suction head, the handle further comprising a plurality of longitudinally spaced ribs extending from the stem around the stem,
- wherein the articulating joint is a living hinge,
- wherein the plurality of longitudinally spaced ribs are spaced relative to each other along the longitudinal axis, and
- wherein the plurality of longitudinally spaced ribs extend varying lengths from the stem to form a contoured grip profile shaped to match a contour of the user's hand in both the first and second gripping positions.

16. The surgical device for engaging patient tissue via negative pressure from a negative pressure source of claim 15, further comprising the vacuum fitting having an open end in fluid communication with the suction chamber, the vacuum fitting configured to couple to the negative pressure source.

17. The surgical device for engaging patient tissue via negative pressure from a negative pressure source of claim 16, wherein the living hinge is an annular living hinge, wherein the annular living hinge includes joint side walls of a first thickness and the stem includes stem side walls of a second thickness, and wherein the second thickness of the stem side walls is greater than the first thickness of the joint side walls.

18. The surgical device for engaging patient tissue via negative pressure from a negative pressure source of claim 17, wherein the stem, the suction head, the handle, the fitting, and the articulating joint are injection molded and are an integral unit.

* * * * *